United States Patent
Benowitz et al.

(10) Patent No.: US 7,666,843 B2
(45) Date of Patent: *Feb. 23, 2010

(54) METHODS AND COMPOSITIONS FOR TREATMENT OF NEUROLOGICAL DISORDER

(75) Inventors: Larry I. Benowitz, Newton, MA (US); Carleen Ann Irwin, Chestnut Hill, MA (US)

(73) Assignee: Children's Medical Center Corporation, Boston, MA (US)

( * ) Notice: Subject to any disclaimer, the term of this patent is extended or adjusted under 35 U.S.C. 154(b) by 169 days.

This patent is subject to a terminal disclaimer.

(21) Appl. No.: 10/528,685

(22) PCT Filed: Sep. 25, 2003

(86) PCT No.: PCT/US03/30466

§ 371 (c)(1),
(2), (4) Date: Jul. 18, 2005

(87) PCT Pub. No.: WO2004/028468

PCT Pub. Date: Apr. 8, 2004

(65) Prior Publication Data

US 2005/0256059 A1    Nov. 17, 2005

Related U.S. Application Data

(60) Provisional application No. 60/414,063, filed on Sep. 27, 2002.

(51) Int. Cl.
*A61K 31/70* (2006.01)
(52) U.S. Cl. ...................................................... 514/23
(58) Field of Classification Search .................. 514/23
See application file for complete search history.

(56) References Cited

U.S. PATENT DOCUMENTS

| 4,471,114 A * | 9/1984 | Sherman et al. ............. 536/127 |
| 5,242,932 A | 9/1993 | Gandy et al. |
| 5,604,202 A | 2/1997 | Kessler et al. |
| 6,855,690 B2 * | 2/2005 | Benowitz ........................ 514/2 |
| 7,238,529 B2 * | 7/2007 | Benowitz et al. ............... 514/12 |

FOREIGN PATENT DOCUMENTS

| CA | 2103399 A1 | 5/1995 |
| CA | 2182731 A1 | 8/1995 |
| CA | 2411666 A1 | 12/2001 |
| CA | 2482746 A1 | 11/2003 |
| DE | 39 35 906 C2 | 5/1991 |
| DE | 3935906 A1 | 5/1991 |
| GB | 2299025 * | 9/1996 |
| GB | 2299025 A | 9/1996 |
| WO | 02/087557 A1 | 11/2002 |
| WO | WO 02/087557 A | 11/2002 |

OTHER PUBLICATIONS

Benowitz, L.I. et al., The Journal of Biological Chemistry, vol. 273 (No. 45), p. 29626-29634, (Nov. 6, 1998).
Berry, M. et al., Journal of Neurocytology, 25:147-170, (1996).
Fischer, D. et al., Investigative Ophthalmology & Visual Science, vol. 41 (No. 12), p. 3943-3954, (Nov. 2000).
Fischer, D. et al., Experimental Neurology, 172:257-272, (2001).
Goldberg, J.L. et al., Neuron, 33:689-702, (Feb. 28, 2002).
Leon, S. et al., The Journal of Neuroscience, vol. 20 (No. 12), p. 4615-4626, (Jun. 15, 2000).
Meyer-Franke, A. et al., Neuron, 15:805-819, (Oct. 1995).
Petrausch, B. et al., The Journal of Neuroscience, vol. 20 (No. 21), p. 8031-8041, (Nov. 1, 2000).
Schwalb, J.M. et al., Neuroscience, vol. 72 ( No. 4), p. 901-910, (1996).
Schwalb, J.M. et al., The Journal of Neuroscience, vol. 15 (No. 8), p. 5514-5525, (Aug. 1995).
Shen, S. et al., Neuron, 23:285-295, (Jun. 1999).
Yin, Y. et al., The Journal of Neuroscience, vol. 23 (No. 6), p. 2284-2293, (Mar. 15, 2003).

* cited by examiner

*Primary Examiner*—Shaojia Anna Jiang
*Assistant Examiner*—Ganapathy Krishnan
(74) *Attorney, Agent, or Firm*—Nixon Peabody LLP

(57) ABSTRACT

The present invention provides methods and compositions for producing a neurosalutary effect in a subject useful in treatment of neurological disorders, including retinal and optic nerve damage, in a subject in need thereof. The method includes administering to a subject a therapeutically effective amount of a hexose, such as mannose.

6 Claims, 14 Drawing Sheets

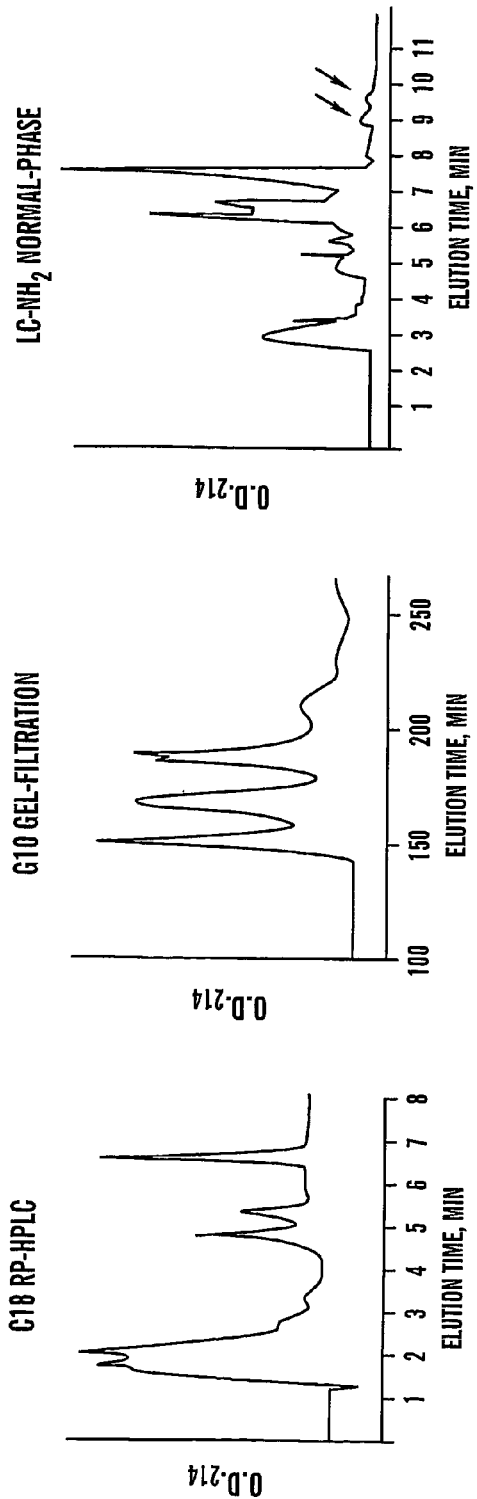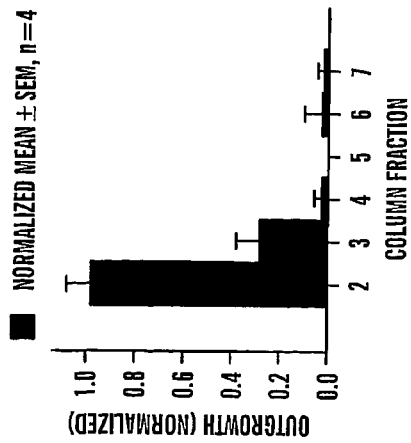

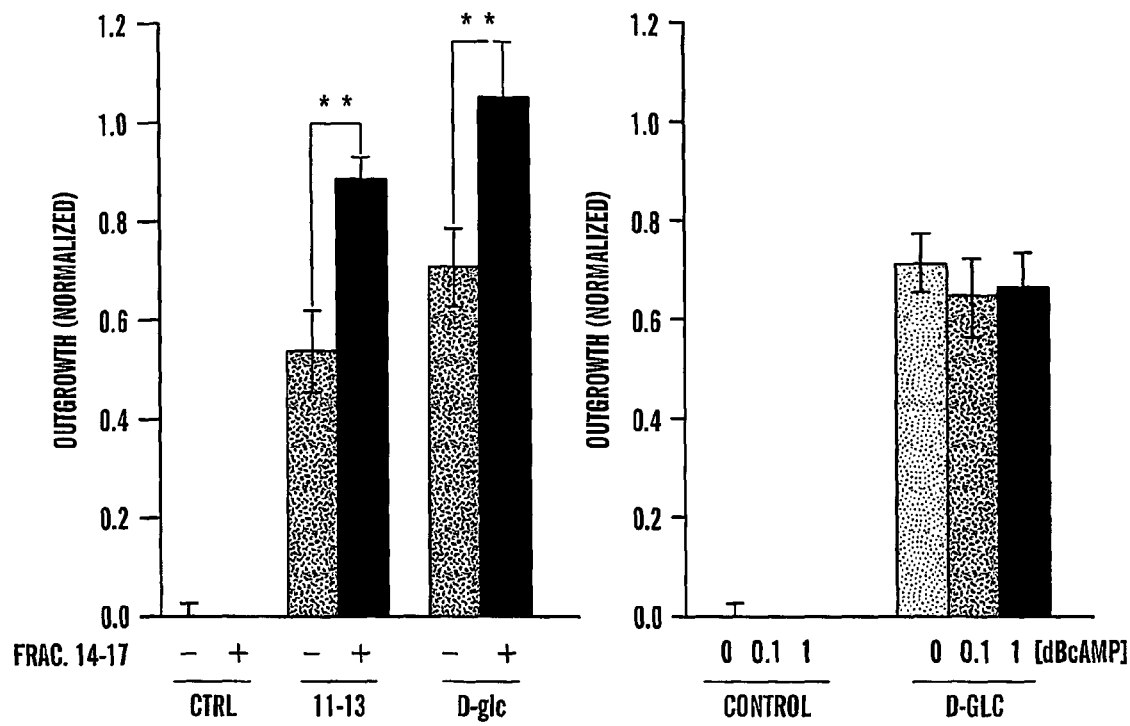
FIG. 7D  FIG. 7E
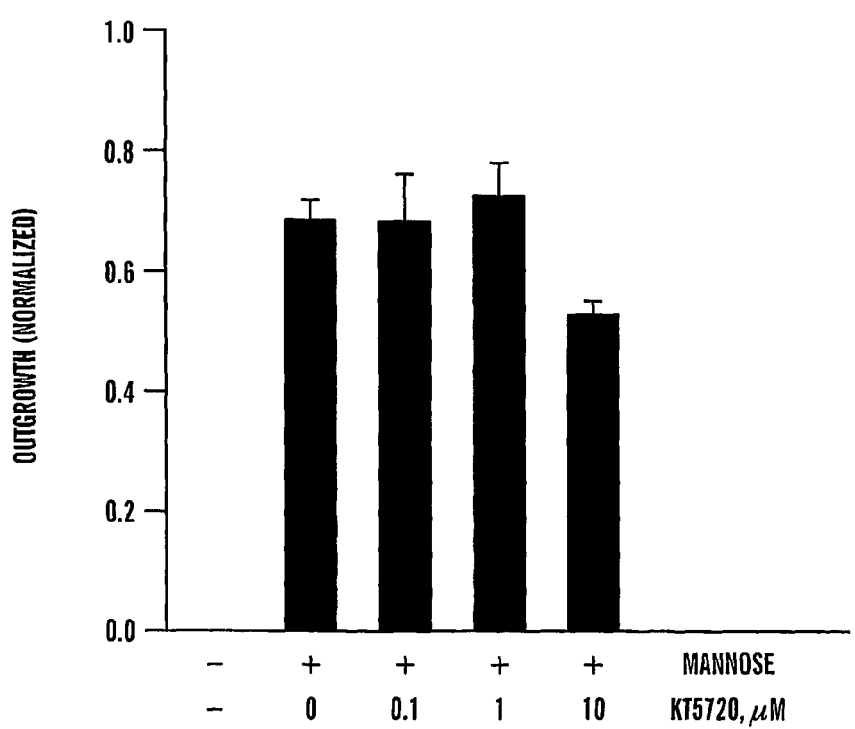
FIG. 7F

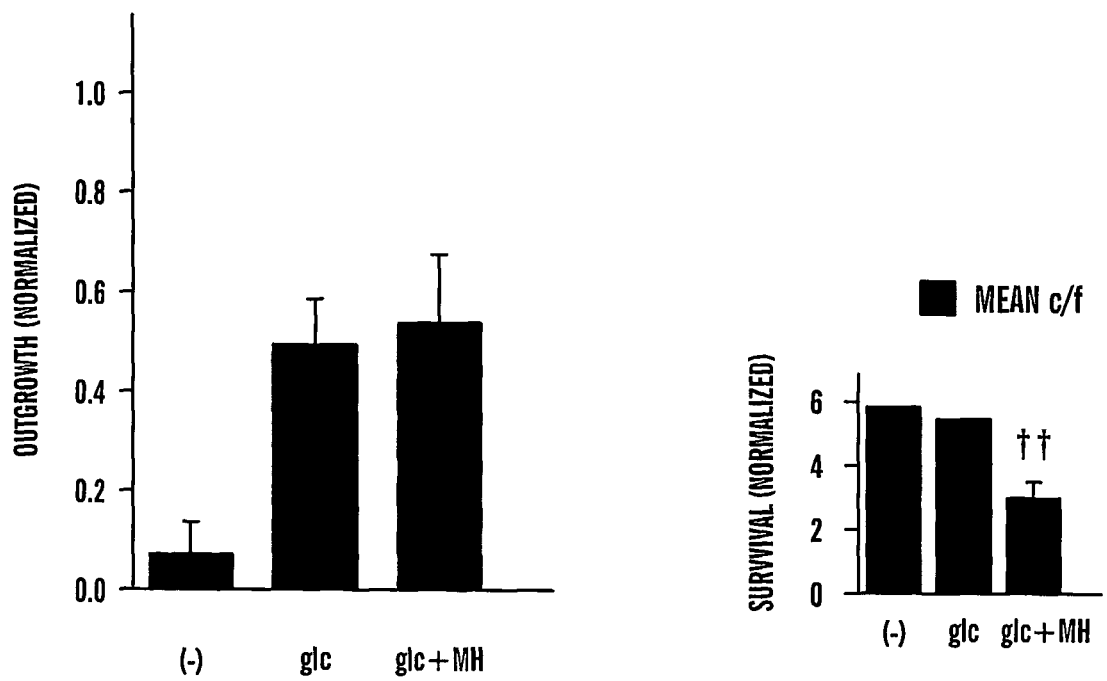
FIG. 8D  FIG. 8E
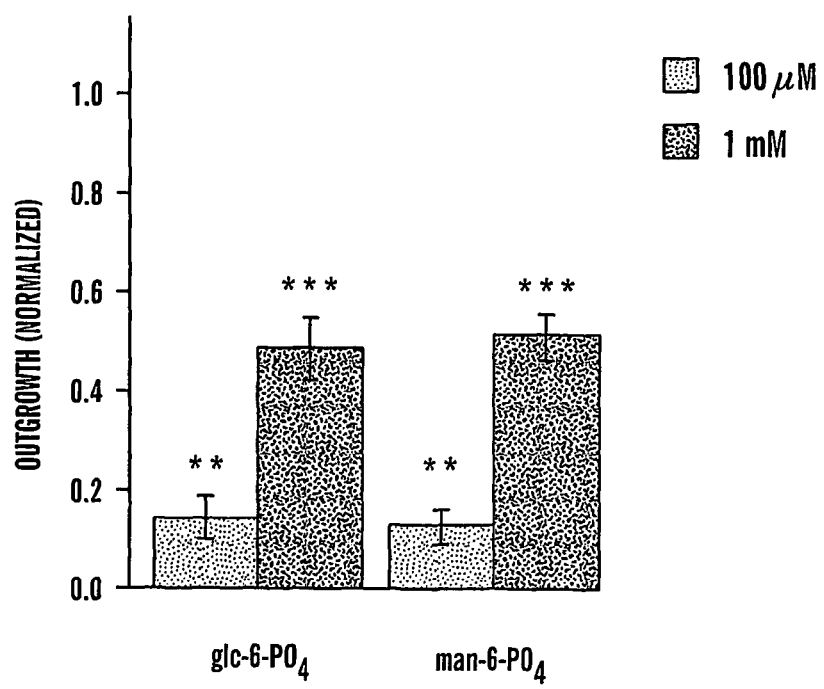
FIG. 8F

METHODS AND COMPOSITIONS FOR TREATMENT OF NEUROLOGICAL DISORDER

CROSS-REFERENCE TO RELATED APPLICATIONS

This application is a 371 National Stage of International Application No. PCT/US2003/030466 filed on Sep. 25, 2003, which designated the U.S., and which claims the benefit under 35 U.S.C. § 119 (e) of U.S. Provisional Application No. 60/414,063 filed on Sep. 27, 2002.

BACKGROUND OF THE INVENTION

Nerves in mature mammals, such as the optic nerve, do not normally regenerate after injury. Retinal ganglion cells (RGCs) initiate a sprouting reaction at their damaged nerve endings, but this growth is abortive and the cells soon begin to die (Ramon y Cajal, 1991). Nonetheless, RGCs can regenerate lengthy axons through a peripheral nerve graft (Aguayo et al., 1991) and even through the optic nerve itself if the lens is injured (Fischer et al., 2000; Leon et al., 2000), or if a fragment of peripheral nerve is implanted into the vitreous (Berry et al., 1996). These latter manipulations lead to the appearance of activated macrophages in the eye, and it has been recently shown that intravitreal macrophage activation is sufficient to allow RGCs to regenerate their axons through the optic nerve (Leon et al., 2000; Yin et al., 2003). In culture, a macrophage-derived protein, acting in concert with a small molecule that is constitutively present in the vitreous, stimulates mature rat RGCs to regenerate their axons in a cAMP-dependent fashion (Yin et al., 2003).

In contrast to mammals, fish and amphibia can regenerate their optic nerves throughout life (Jacobson, 1991). In culture, the most potent axon-promoting factor for goldfish RGCs is a small hydrophilic molecule (<500 Daltons) that is secreted by non-neuronal cells of the optic nerve. This molecule is referred to as AF-1 (Schwalb et al., 1995; Schwalb et al., 1996).

Understanding the factors involved in mammalian and non-mammalian neuron regeneration will aid in the development of potential therapeutics for treatment of neuronal disorders. Disorders of the peripheral and central nervous system are widespread, and for many of these conditions effective therapeutic interventions are lacking. Neurological disorders may be caused by an injury to a neuron, such as a mechanical injury or an injury due to a toxic compound, by the abnormal growth or development of a neuron, or by the misregulation (such as downregulation or upregulation) of an activity of a neuron. There is a need in the art for methods and compositions that can improve the ability of a neuron, or portion of the nervous system, to resist insult, to regenerate, and to maintain desirable function, which can be used for treatment of neurological disorders.

SUMMARY OF THE INVENTION

The present invention provides methods and compositions for producing a neurosalutary effect in a subject with a neurological condition; such effects include promoting neuronal survival, axonal outgrowth, neuronal regeneration or normalized neurological function in a subject.

In one aspect, the present invention provides a method which includes administering to a subject a therapeutically effective amount of a hexose (e.g., mannose) or a hexose derivative, thereby producing a neurosalutary effect in the subject.

In another embodiment, the present invention provides treatment of neurological disorders, including retinal and optic nerve damage, in a subject by administering to a subject in need of such treatment an effective amount of a hexose or a hexose derivative.

In other embodiments, the methods of the invention further include administering to a subject a cAMP modulator and/or a macrophage-derived factor.

In one aspect, the hexose or hexose derivative is administered to a subject in accordance with the present invention such that the hexose is brought into contact with neurons of the central nervous system of the subject. For example, the hexose may be administered into the cerebrospinal fluid of the subject into the intrathecal space by introducing the hexose into a cerebral ventricle, the lumbar area, or the cisterna magna. In such circumstances, the hexose can be administered locally to cortical neurons or retinal ganglion cells to produce a neurosalutary effect.

In certain embodiments, the pharmaceutically acceptable formulation provides sustained delivery, providing effective amounts of the hexose to a subject for at least one week; or in other embodiments, at least one month, after the pharmaceutically acceptable formulation is initially administered to the subject. Approaches for achieving sustained delivery of a formulation of the invention include the use of a slow release polymeric capsule, a bioerodible matrix, or an infusion pump that disperses the hexose or other therapeutic compound of the invention. The infusion pump may be implanted subcutaneously, intracranially, or in other locations as would be medically desirable. In certain embodiments, the therapeutic factors or compositions of the invention would be dispensed by the infusion pump via a catheter either into the cerebrospinal fluid, or to a site where local delivery was desired, such as a site of neuronal injury or a site of neurodegenerative changes.

Pharmaceutical compositions that include a hexose derivative and a pharmaceutically acceptable carrier may be packed with instructions for use of the pharmaceutical composition for treating a neurological disorder. In one embodiment, the pharmaceutical composition further includes a cAMP modulator and/or a macrophage-derived factor.

Other features and advantages of the invention will be apparent from the following detailed description, and from the claims.

BRIEF DESCRIPTION OF THE FIGURES

FIG. 1A shows molecules present in either the normal rat vitreous or in the vitreous one week after lens injury were extracted into saline; molecules<3 kDa in size were separated by ultrafiltration and tested for axon-promoting activity using goldfish retinal ganglion cells. When present at either 1.25% or 5% of their original concentration, the low molecular weight extract induced as much outgrowth as inosine, and this was independent of whether or not the lens was injured. Outgrowth data are normalized by subtracting the level of growth in culture media alone and then dividing by the net growth in the positive controls. FIG. 1B illustrates cell survival. The number of retinal ganglion cells per 200× microscope field was unaltered by any of the manipulations.

Axon growth induced by the low molecular weight factor from the vitreous extract (VE<3) is inhibited completely by the purine analog 6-thioguanine (6-TG) but is not affected by an inhibitor of purine transport, NBTI. These agents exert similar effects on outgrowth induced by AF-1, a small factor derived from goldfish optic nerve conditioned media. In contrast, growth stimulated by inosine is only partially inhibited by 6-TG and is blocked completely by NBTI.

Figure 3A:
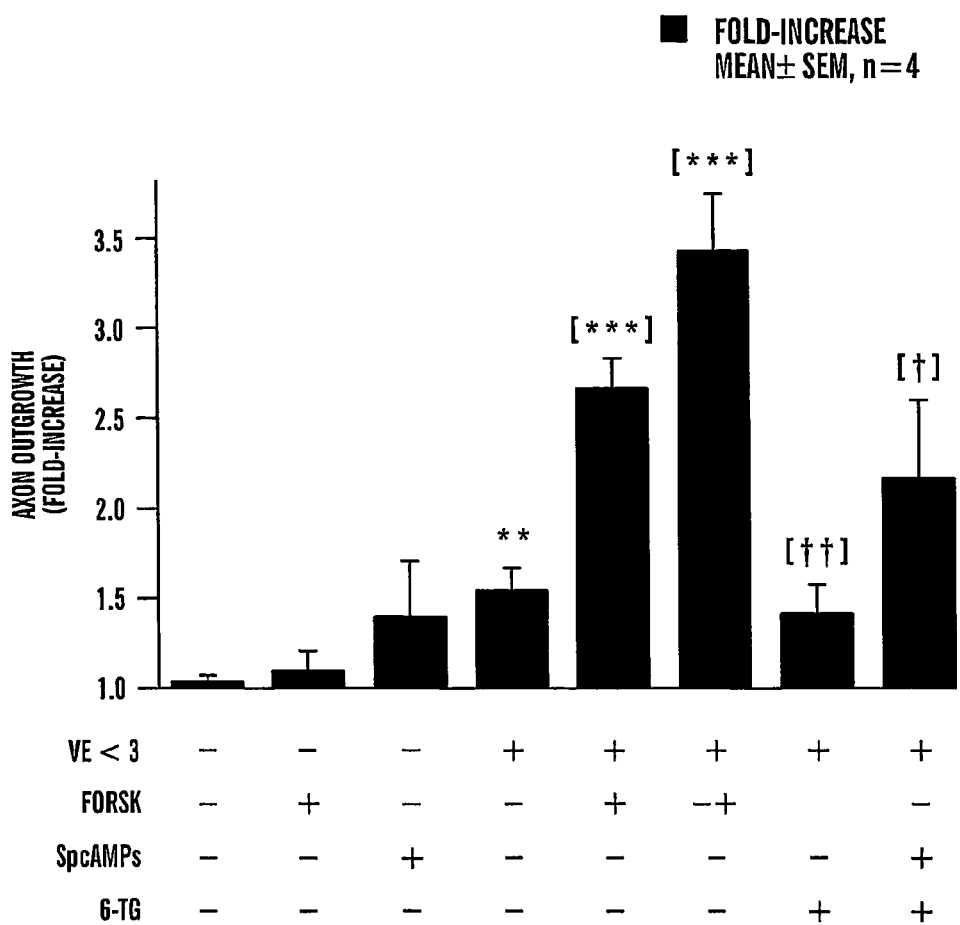
Figure 3B:
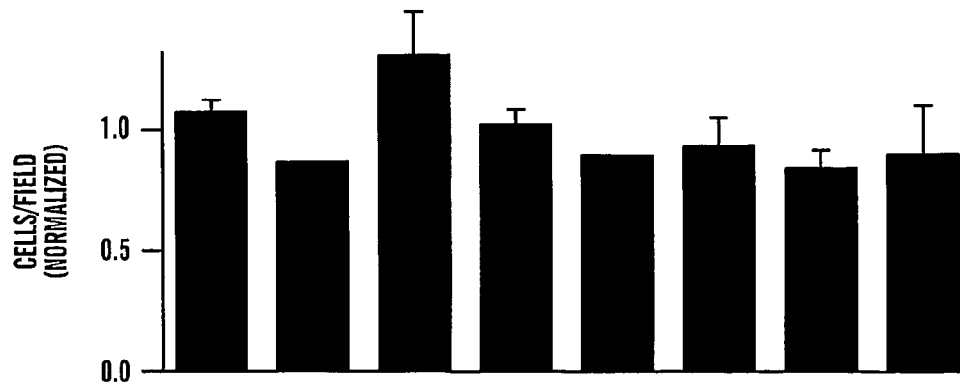
Figure 3C:
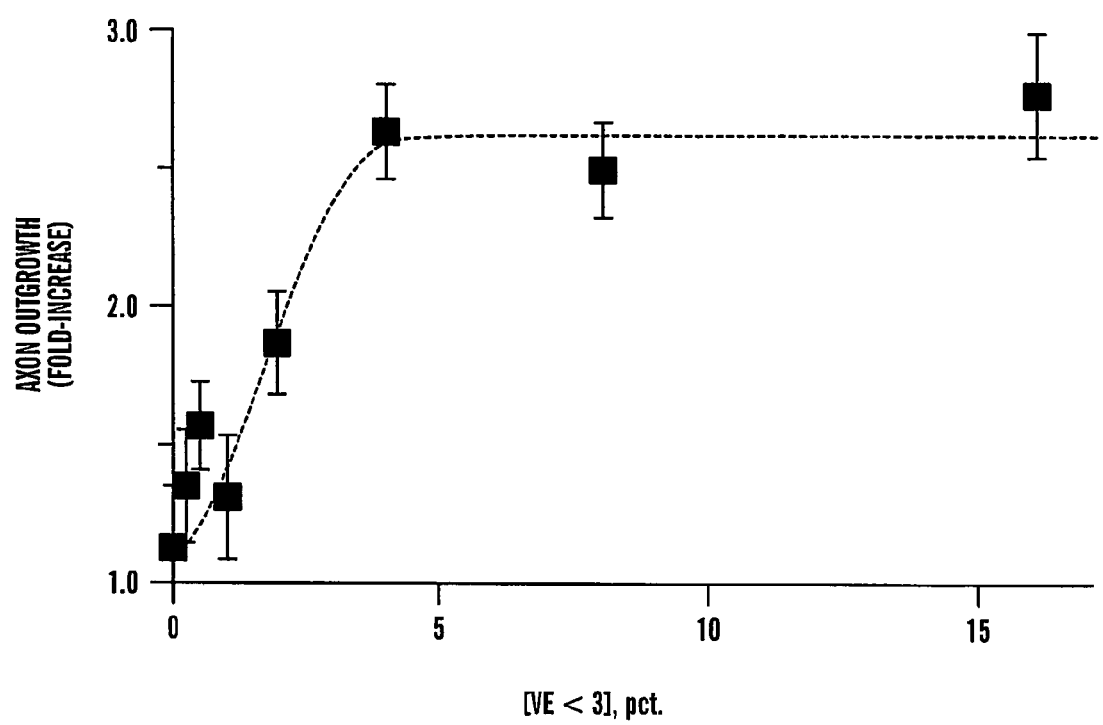

FIGS. 3A-C show that the vitreous-derived factor stimulates axon growth in rat retinal ganglion cells in a cAMP-dependent fashion. FIG. 3A shows axon outgrowth. By itself, the low molecular weight factor from the vitreous has a small but significant axon-promoting effect on rat retinal ganglion cells in culture. The addition of either forskolin (forsk) or the PKA agonist Sp-cAMP-s strongly potentiates this effect. This growth is strongly inhibited by 6-TG. Results are normalized to the level of growth seen in control cultures grown in media alone (in the range of 8-12% of cells extending axons>2 cell diameters in length). FIG. 3B shows cell survival. None of the agents tested altered RGC survival. $p<0.01$ compared to negative control; [*]$p<0.001$ compared to growth in cultures treated with PKA agonists alone; [††]$p<0.01$ compared to growth in cultures treated with VE<3 plus the PKA agonists. FIG. 3C shows VE<3 gives a near-maximal response at a concentration of 5%. $p<0.01$ compared to negative control; [*]$p<0.001$ compared to either negative controls or cells treated with PKA agonists alone.

Figure 4:
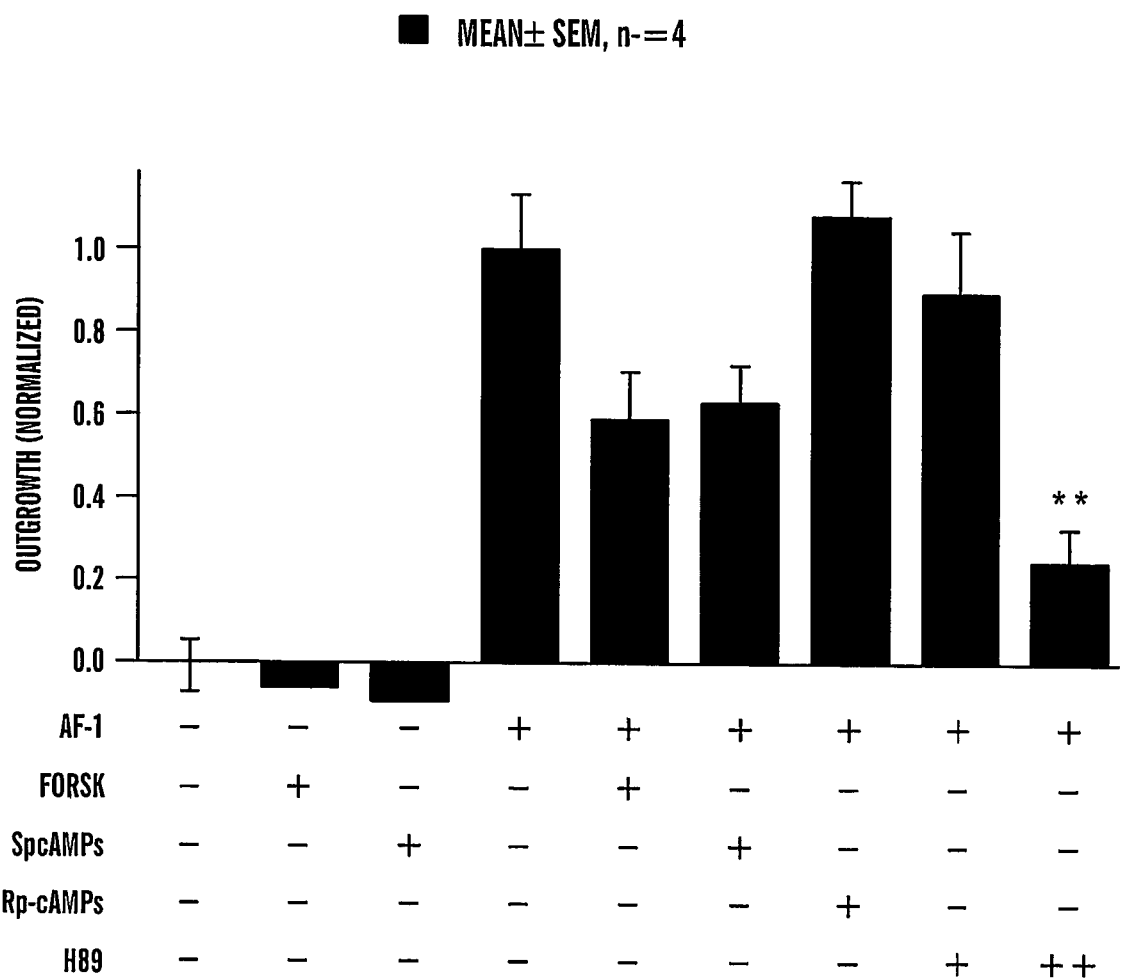

FIG. 4 shows axon growth in goldfish RGCs is not enhanced by elevating intracellular cAMP levels. Neither forskolin nor Sp-cAMP-s by itself stimulated axon growth in goldfish RGCs, and reduced the level of outgrowth induced by AF-1. The PKA antagonists Rp-cAMP-s or H-89 (at 5 µM) did not reduce AF-1 induced growth, although higher concentrations of H89 (20 µM) did. **$p<0.01$ (significance of reduction compared to growth with AF-1 alone).

FIGS. 5A-F illustrate isolation of the small vitreous-derived growth factor. FIGS. 5A and B show reversed-phase HPLC. The low molecular weight factor from bovine vitreous was concentrated, extracted into 95% ethanol, and subjected to HPLC on a C-18 reversed-phase column. The axon promoting activity eluted in the earliest peak. FIGS. 5C and D show gel filtration chromatography. On a G-10 Sephadex column, the axon-promoting activity eluted as a coherent peak that included high levels of material showing adsorbance at 214 nm.

FIGS. 5E and F show normal-phase chromatography. The peak containing the axon-promoting activity from the gel-filtration column was separated on a LC-NH$_2$ normal-phase column using HPLC. The axon-promoting activity eluted later than most components with absorbance at 214 nm (arrows). Bioassays in all cases were carried out on goldfish retinal ganglion cells.

Figure 6A:
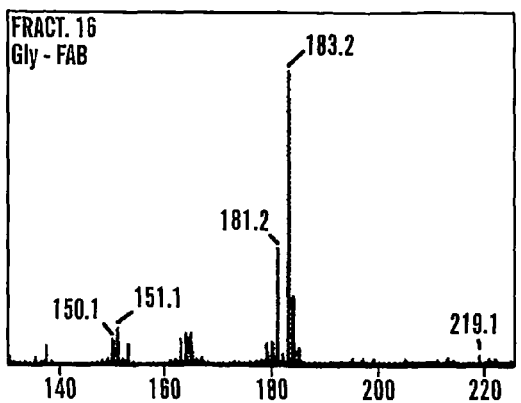
Figure 6B:
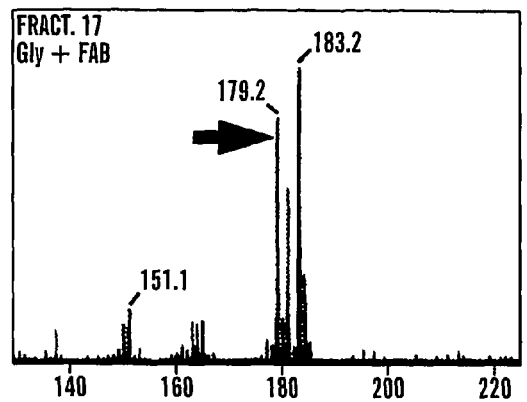
Figure 6C:
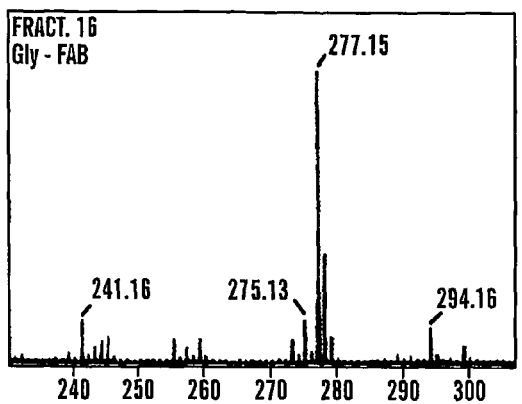
Figure 6D:
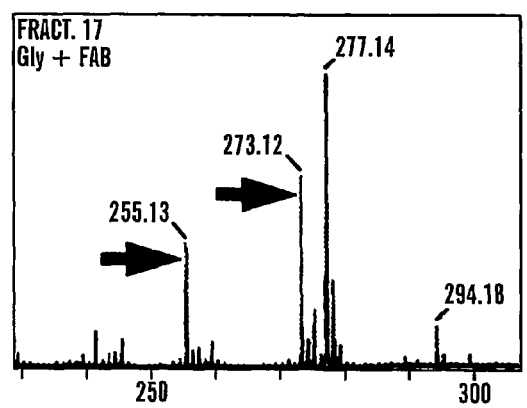
Figure 6E:
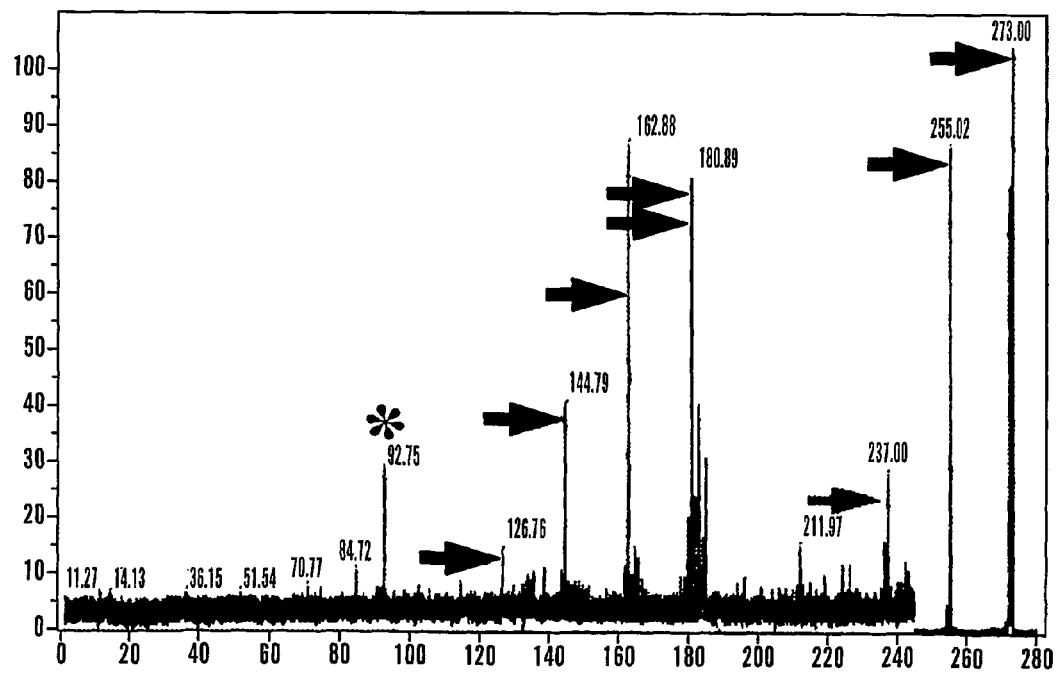

FIGS. 6A-E show identification of the axon-promoting factor by mass spectrometry. FIGS. 6A and B show fast atomic bombardment mass spectra in the negative ion mode in the range of m/z=140 to 220 of a fraction from the LC-NH$_2$ column that does not induce axon growth (6A) and the adjacent fraction that stimulates axon growth (6B). Spectra were carried out in the presence of glycerol. Only the active fraction contains a peak with m/z=179.2 (arrow in b). Because the ion masses in the negative mode represent the masses minus one proton, the actual mass of the species present in the active fraction would be expected to be 180. FIGS. 6C and D show fast atomic bombardment mass spectra in the positive ion mode in the range of m/z=230 to 300 of a fraction from the LC-NH$_2$ column that does not induce axon growth (6C) and the adjacent fraction that stimulates axon growth (6D). Spectra were carried out in the presence of glycerol. Only the active fraction contains peaks with m/z=273.12 and 255.13 (arrows). Because the ion masses in the positive mode represent the masses plus one proton, and because these ions may include adducts with glycerol (mass=92), the actual masses of the species present in the active fraction could be 180.13 and 162.12. FIG. 6E shows mass spectrum of the m/z=273 species from (6D) subjected to MS/MS analysis in the positive ion mode in the presence of glycerol. When subjected to higher voltage, the m/z 273 species generated a glycerol peak (m/z=93, red asterisk) and an ion of m/z=181 (double arrows), i.e., the parent species minus glycerol; most of the additional ions represent successive losses of 18 amu from either the 181 ion (m/z=163, 145 and 127, arrows) or from the glycerol adduct of the 181 species (m/z=255, 237, arrows). These results indicate that the axon-promoting factor is a hexose sugar with the formula $C_6H_{12}O_6$.

Figure 7A:
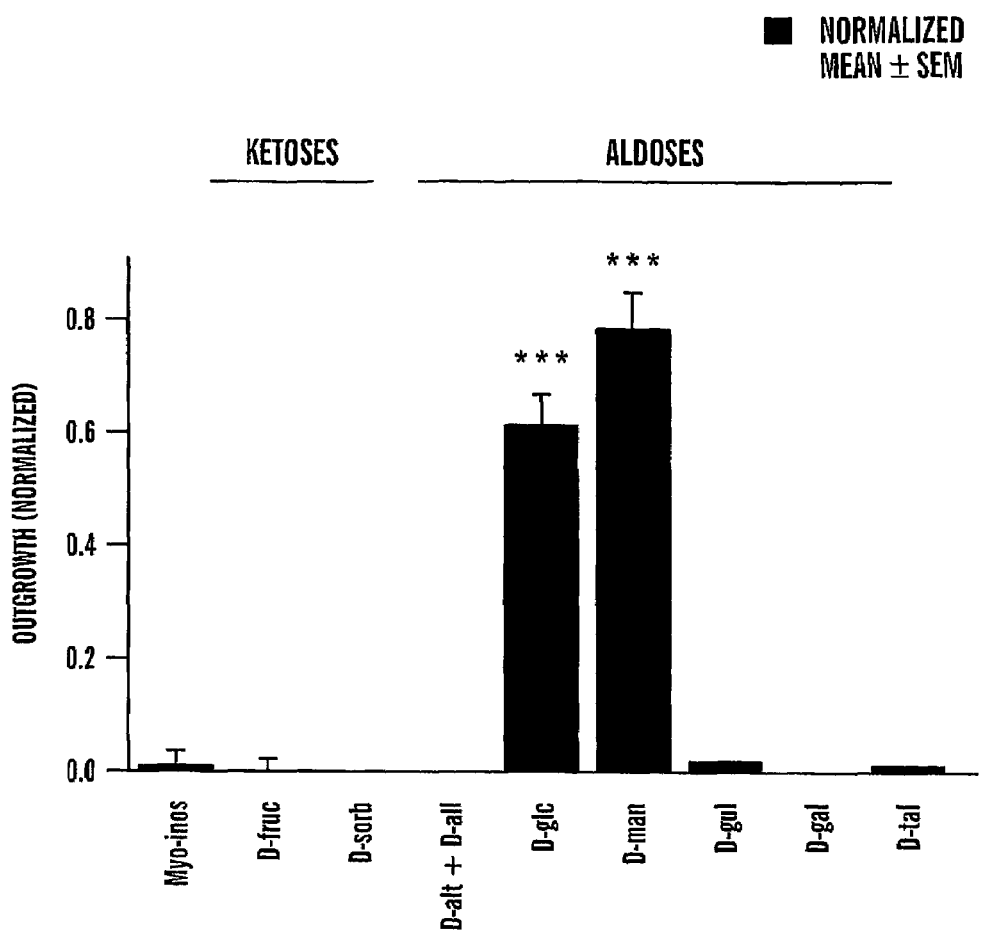
Figure 7B:
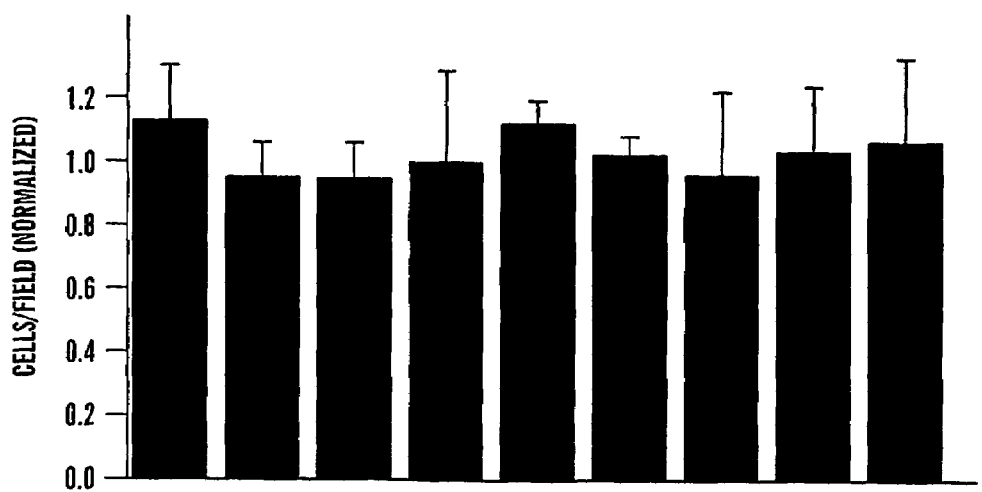
Figure 7C:
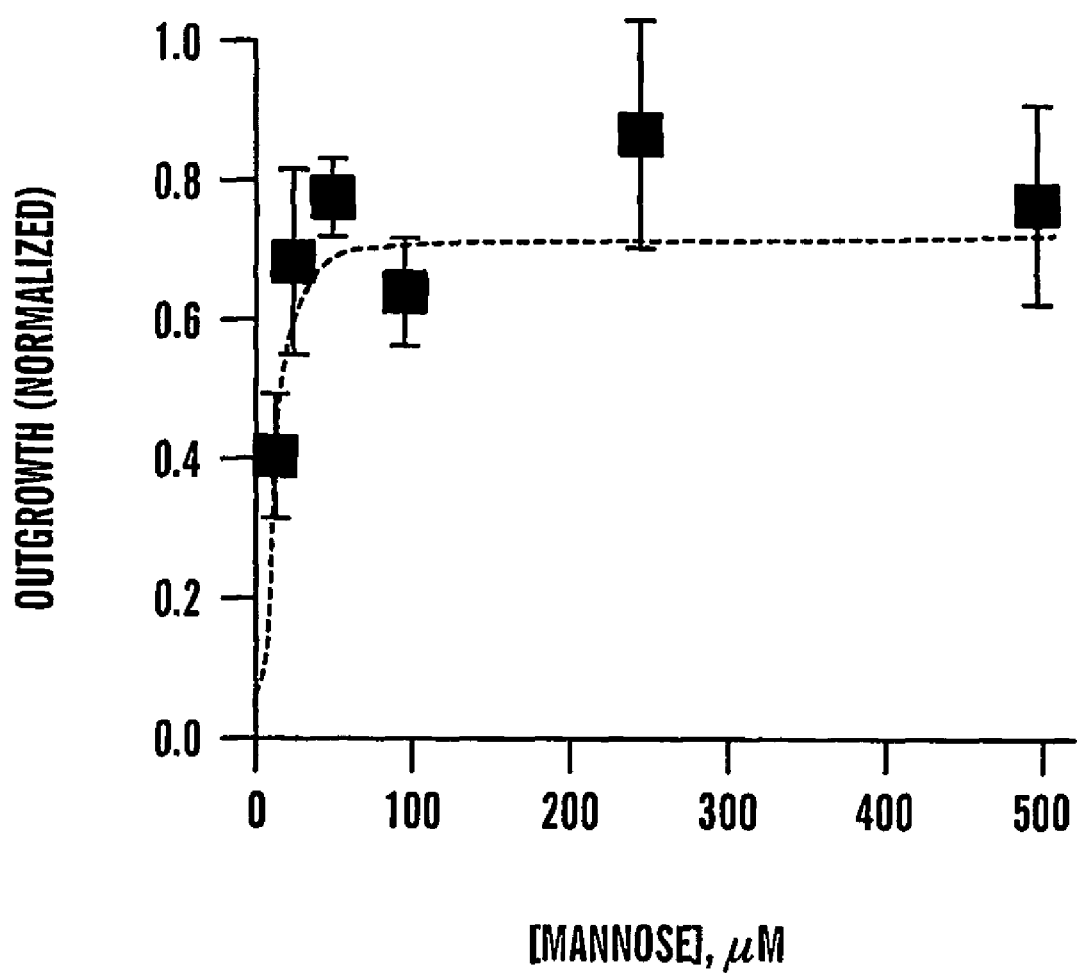

FIGS. 7A-F show that goldfish RGCs regenerate their axons in response to D-glucose and D-mannose. FIG. 7A shows outgrowth in response to monosaccharides. Of the many hexose sugars tested, only glucose (glc) and mannose (man) induced axon growth. Other monosaccharides tested include myo-inositol (myo-inos), fructose (fruc), sorbose (sorb), altrose (alt), allose (all), gulose (gul), galactose (gal) and talose (tal), all at 50 or 100 µM and all in the D-configuration. FIG. 7B shows cell survival. The effects of mannose and glucose on axon regeneration are not related to any changes in cell survival. FIG. 7C shows a dose-response curve for mannose. The effect of mannose on axon outgrowth saturates at 25-50 µM, and the $ED_{50}$ is approximately 10 µM. FIG. 7D shows the effect of mannose is enhanced by a factor which itself has no axon-promoting effects. By itself, D-glc stimulates only about 70% the level of axon growth seen with the vitreous extract. A fraction that elutes later from the gel-filtration column (14-17) has no activity by itself, but enhances the effect of glucose back to the level of the unfractionated vitreous extract.

FIG. 7E shows that the membrane-permeable cAMP analog, dBcAMP (1 mM) does not augment the effect of glucose on goldfish retinal ganglion cells. FIG. 7F shows that the protein kinase A inhibitor KT5720 has little effect on mannose-induced growth in goldfish retinal ganglion cells.

Figure 8A:
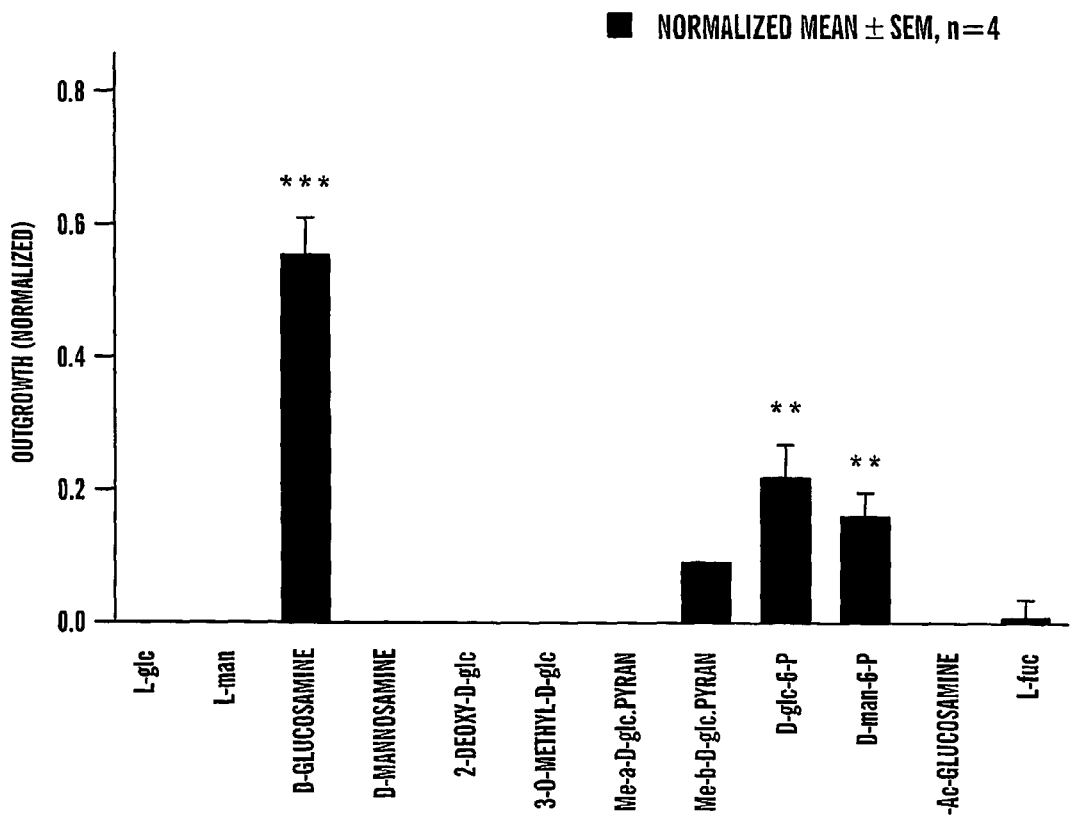
Figure 8B:
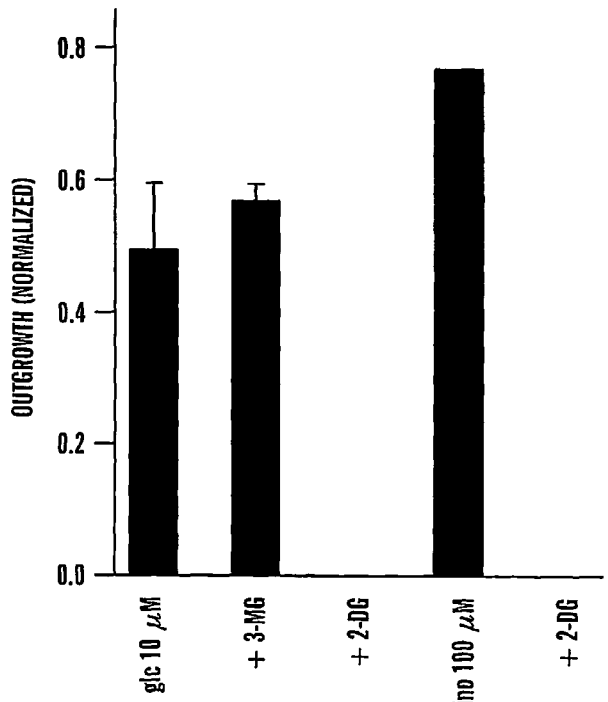
Figure 8C:
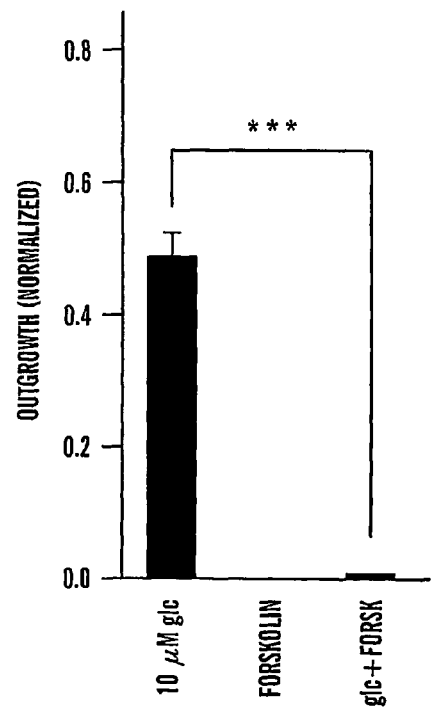

FIGS. 8A-E show effects of various glucose analogs and inhibitors on axon growth. FIG. 8A shows the stereospecificity of the effects seen with D-mannose and D-glucose as demonstrated by the inactivity of the L-enantiomers (100 µM). D-glucosamine (25 µM), an glucose analog with an amino group substituted for the hydroxyl group at C-2, is strongly active, whereas mannosamine is not. No activity is seen with 2-deoxy-D-glucose (1 mM), 3-O-methyl-D-glucose, methyl-α- or methyl-β-glucose pyranose, N-acetyl-glucosamine (N-Ac-glucosamine) or L-fucose. However, the non-membrane-permeable 6-phosphates of glucose and mannose (D-glc-6-P, D-man-6-P) induce a small but statistically significant level of outgrowth. $p<0.01$ relative to control cells grown in media alone; *$p<0.001$ relative to negative controls. FIG. 8B shows that forskolin diminishes the effect of D-glucose. Outgrowth induced by 10 µM glucose is inhibited by forskolin (10 µM). ***$p<0.001$ compared to growth induced by glucose alone. FIG. 8C shows 3-O-MG, a non-metabolized glucose analog and inhibitor of glucose transport, fails to block the effect of glucose (10 µM). Another inhibitor of glucose transport, 2-DG, does block the effect of glucose, but this effect may be nonspecific, because it also blocks the effect of inosine. FIG. 8D shows that mannoheptulose (MH, 10 mM), an inhibitor of both glucose-6 kinase and hexose-6 kinase, has no effect on outgrowth induced by glucose or mannose, despite being detrimental to cell survival as shown in FIG. 8E where MH decreases cell survival (c/f, viable RGCs per field).

FIG. 8F shows that extracellular D-glucose-6-phosphate and D-mannose-6-phosphate stimulate a modest amount of outgrowth at 100 μM (p<0.01), and appreciable growth at 1 mM. The y-axis is the same as in (b). p<0.01, *p<0.001 relative to cells grown in media alone: ††p<0.01 (decrease in survival relative to glucose alone).

Figure 9A:
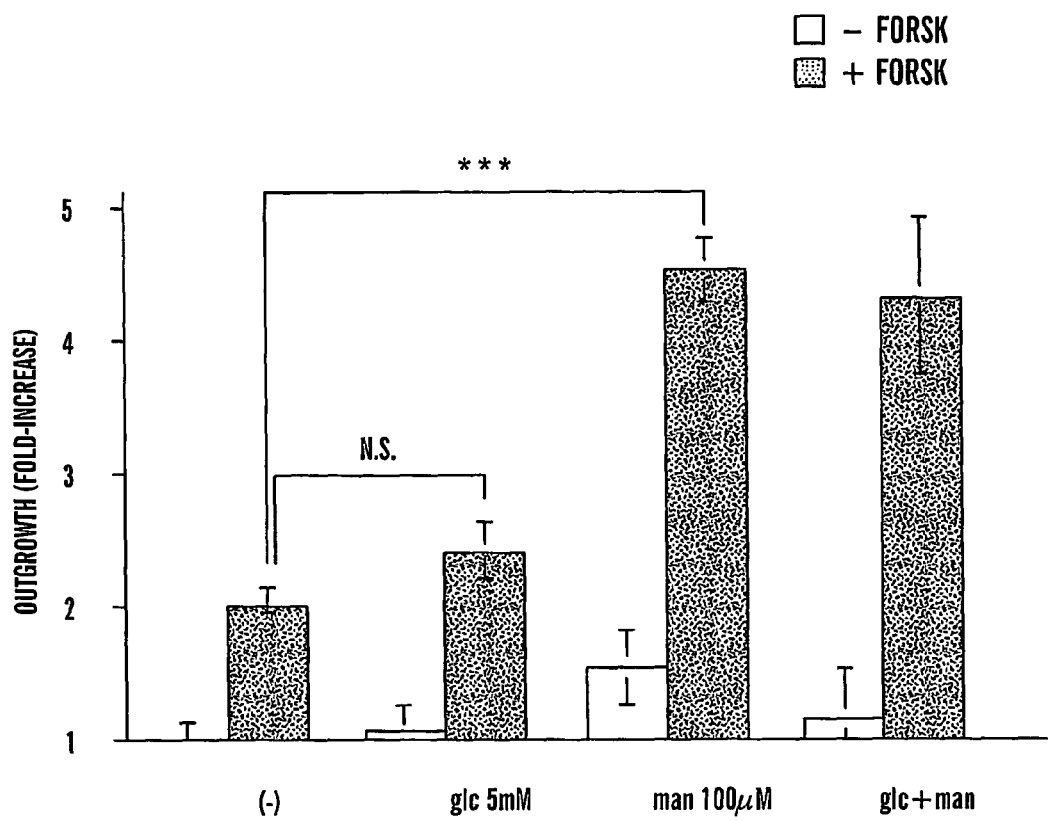
Figure 9B:
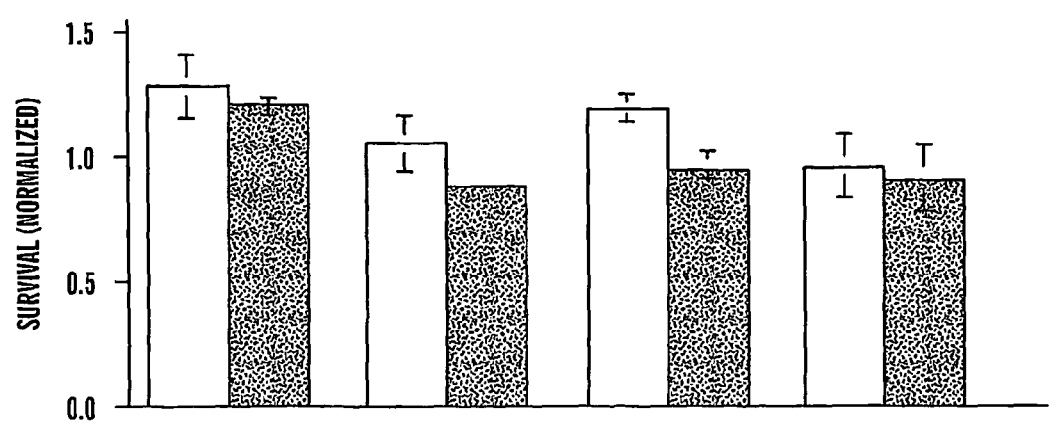
Figure 9C:
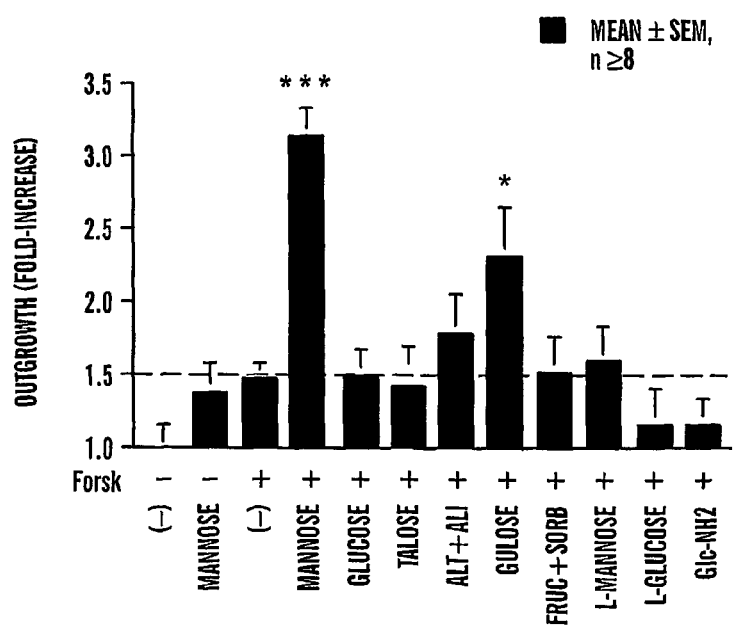
Figure 9D:
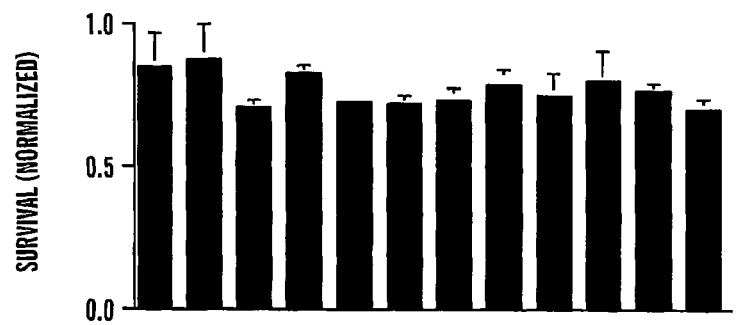
Figure 9E:
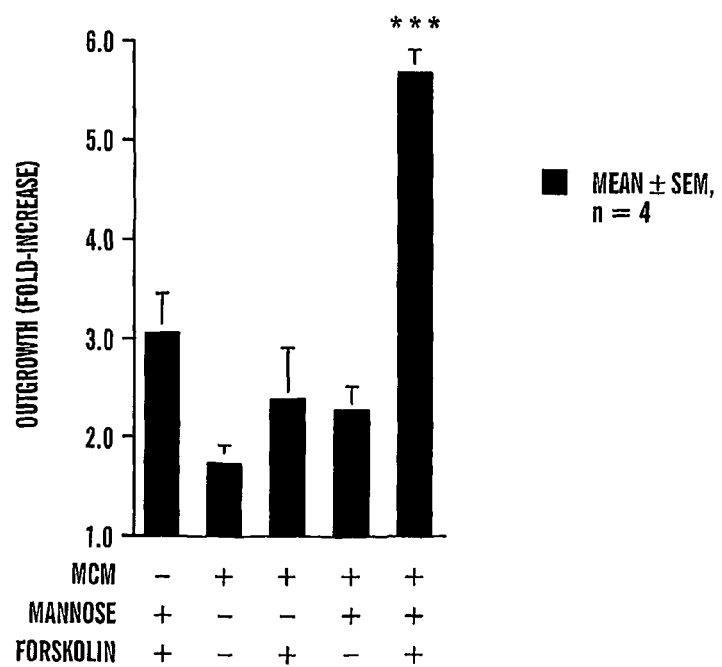

FIGS. 9A-E show rat retinal ganglion cells respond selectively to mannose in a cAMP-dependent manner. FIG. 9A shows axon outgrowth. Mannose induced a small, marginally significant level of outgrowth, whereas forskolin (5 μM) by itself produced a somewhat larger effect. In the presence of forskolin, mannose induced a striking increase in outgrowth; glucose at physiological concentrations (5 mM) did not. The effect of mannose was at least as great as that of the low molecular extract from the vitreous, and was not altered by the addition of glucose. These studies were carried out in the presence of 5% fetal bovine serum in the culture media. [*]p=0.05 compared to negative control, 1-tailed t-test; p<0.01 compared to negative control, 2-tailed t-test. *p<0.001; n.s.=not significant relative to growth induced by forskolin alone. FIG. 9B shows cell survival. The effect of mannose and forskolin on axon outgrowth is independent of any changes in cell survival. FIG. 9C shows mature rat RGCs respond strongly to mannose in the presence of forskolin. Glucose is inactive. All sugars are in the D-configuration unless noted otherwise. (*)p<0.05 compared to negative control; *p<0.05, *p<0.001 compared to forskolin alone (dotted line). FIG. 9D shows cell survival is unaffected by any of the carbohydrates. The numbers of viable RGCs per field are normalized to the value in negative controls. FIG. 9E shows proteins (>3 kDa) secreted by activated macrophages enhance the effects of mannose. *p<0.001 compared to any of the other conditions.

DETAILED DESCRIPTION OF THE INVENTION

The present invention provides methods and compositions for producing a neurosalutary effect in a subject useful in treatment of neurological disorders, including nerve damage. The method includes administering to a subject a therapeutically effective amount of a hexose (e.g., mannose) or a hexose derivative.

As used herein, the term "hexose" includes any hexose, or derivative thereof, that is able to produce a neurosalutary effect. Preferred hexoses include D-mannose and gulose. The term "hexose derivative" refers to a hexose molecule that has one or more residues (e.g. esters, ethers, amino groups, amido groups, phosphate groups, sulphate groups, carboxyl groups, carboxy-alkyl groups, and combinations thereof) covalently or ionically attached to one or more of the molecules hydroxyl groups and able to produce a neurosalutary effect. A preferred derivative includes glucose-6-phosphate. The term hexose derivative includes D- and L-isomers of hexose or hexose derivatives able to produce a neurosalutary effect in a subject. Hexose derivatives are well known in the art and commercially available.

As used herein, a "neurosalutary effect" means a response or result favorable to the health or function of a neuron, of a part of the nervous system, or of the nervous system generally. Examples of such effects include improvements in the ability of a neuron or portion of the nervous system to resist insult, to regenerate, to maintain desirable function, to grow or to survive. The phrase "producing a neurosalutary effect" includes producing or effecting such a response or improvement in function or resilience within a component of the nervous system. For example, examples of producing a neurosalutary effect would include stimulating axonal outgrowth after injury to a neuron; rendering a neuron resistant to apoptosis; rendering a neuron resistant to a toxic compound such as β-amyloid, ammonia, or other neurotoxins; reversing age-related neuronal atrophy or loss of function; or reversing age-related loss of cholinergic innervation.

The term "cAMP modulator" includes any compound which has the ability to modulate the amount, production, concentration, activity or stability of cAMP in a cell, or to modulate the pharmacological activity of cellular cAMP. cAMP modulators may act at the level of adenylate cyclase, upstream of adenylate cyclase, or downstream of adenylate cyclase, such as at the level of cAMP itself, in the signaling pathway that leads to the production of cAMP. Cyclic AMP modulators may act inside the cell, for example at the level of a G-protein such as Gi, Go, Gq, Gs and Gt, or outside the cell, such as at the level of an extra-cellular receptor such as a G-protein coupled receptor. Cyclic AMP modulators include activators of adenylate cyclase such as forskolin; nonhydrolyzable analogues of cAMP including 8-bromo-cAMP, 8-chloro-cAMP, or dibutyryl cAMP (db-cAMP); isoprotenol; vasoactive intestinal peptide; calcium ionophores; membrane depolarization; macrophage-derived factors that stimulate cAMP; agents that stimulate macrophage activation such as zymosan or IFN-y; phosphodiesterase inhibitors such as pentoxifylline and theophylline; specific phosphodiesterase IV (PDE IV) inhibitors; and beta 2-adrenoreceptor agonists such as salbutamol. The term cAMP modulator also includes compounds which inhibit cAMP production, function, activity or stability, such as phosphodiesterases, such as cyclic nucleotide phosphodiesterase 3B. cAMP modulators which inhibit cAMP production, function, activity or stability are known in the art and are described in, for example, in Nano et al., 2000, the contents of which are incorporated herein by reference.

"Phosphodiesterase IV inhibitor" refers to an agent that inhibits the activity of the enzyme phosphodiesterase IV. Examples of phosphodiesterase IV inhibitors are known in the art and include 4-arylpyrrolidinones, such as rolipram (A.G. Scientific, Inc.), nitraquazone, denbufylline, tibenelast, CP-80633 and quinazolinediones such as CP-77059.

"Beta-2 adrenoreceptor agonist" refers to an agent that stimulates the beta-2 adrenergic receptor. Examples of beta-2 adrenoreceptor agonists are known in the art and include salmeterol, fenoterol and isoproterenol.

As used herein, the term "macrophage-derived factor" includes any factor derived from a macrophage that has the ability to produce a neurosalutary effect in a subject. Macrophage-derived factors include, but are not limited to, peptides such as oncomodulin and TGF-β. See, WO 01/091783, the disclosure of which is incorporated herein by reference.

The term "administering" to a subject includes dispensing, delivering or applying an active compound in a pharmaceutical formulation to a subject by any suitable route for delivery of the active compound to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route. A hexose may, for example, be administered to a comatose, anesthetized or paralyzed subject via an intravenous injection or may be administered intravenously to a pregnant subject to produce a neurosalutary effect in the fetus. Specific routes of administration may include topical application (such as by eyedrops, creams or erodible formulations to be placed under the eyelid), intraocular injection into the aqueous or the vitreous humor, injection into the external layers of the eye, such as via subconjunctival injection or subtenon injection, parenteral administration or via oral routes.

As used herein, the language "contacting" is intended to include both in vivo or in vitro methods of bringing a compound of the invention into proximity with a neuron such that the compound can exert a neurosalutary effect on the neuron.

As used herein, the term "effective amount" includes an amount effective, at dosages and for periods of time necessary, to achieve the desired result, such as sufficient to produce a neurosalutary effect in a subject. An effective amount of an active compound as defined herein may vary according to factors such as the disease state, age, and weight of the subject, and the ability of the active compound to elicit a desired response in the subject. Dosage regimens may be adjusted to provide the optimum therapeutic response. An effective amount is also one in which any toxic or detrimental effects of the active compound are outweighed by the therapeutically beneficial effects.

A non-limiting range for a therapeutically effective concentration of active compound, e.g., mannose, is 5 µM to 1 mM. In a preferred embodiment the therapeutically effective concentration of the active compound is 25-500 µM.

A therapeutically effective amount or dosage of an active compound may range from about 0.001 to 30 mg/kg body weight, with other ranges of the invention including about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, and 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an active compound can include a single treatment or a series of treatments. In one example, a subject is treated with an active compound in the range of between about 0.1 to 20 mg/kg body weight, one time per week for between about 1 to 10 weeks, alternatively between 2 to 8 weeks, between about 3 to 7 weeks, or for about 4, 5, or 6 weeks. It will also be appreciated that the effective dosage of an active compound used for treatment may increase or decrease over the course of a particular treatment.

The term "subject" is intended to include animals. In particular embodiments, the subject is a mammal, a human or nonhuman primate, a dog, a cat, a horse, a cow or a rodent.

"Neurological disorder" is intended to include a disease, disorder, or condition which directly or indirectly affects the normal functioning or anatomy of a subject's nervous system. Elements of the nervous system subject to disorders which may be effectively treated with the compounds and methods of the invention include the central, peripheral, somatic, autonomic, sympathetic and parasympathetic components of the nervous system, neurosensory tissues within the eye, ear, nose, mouth or other organs, as well as glial tissues associated with neuronal cells and structures. Neurological disorders may be caused by an injury to a neuron, such as a mechanical injury or an injury due to a toxic compound, by the abnormal growth or development of a neuron, or by the misregulation (such as downregulation or upregulation) of an activity of a neuron. Neurological disorders can detrimentally affect nervous system functions such as the sensory function (the ability to sense changes within the body and the outside environment); the integrative function (the ability to interpret the changes); and the motor function (the ability to respond to the interpretation by initiating an action such as a muscular contraction or glandular secretion). Examples of neurological disorders include traumatic or toxic injuries to peripheral or cranial nerves, spinal cord or to the brain, cranial nerves, traumatic brain injury, stroke, cerebral aneurism, and spinal cord injury. Other neurological disorders include cognitive and neurodegenerative disorders such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, hereditary motor and sensory neuropathy (Charcot-Marie-Tooth disease), diabetic neuropathy, progressive supranuclear palsy, epilepsy, and Jakob-Creutzfieldt disease. Autonomic function disorders include hypertension and sleep disorders. Also to be treated with compounds and methods of the invention are neuropsychiatric disorders such as depression, schizophrenia, schizoaffective disorder, Korsakoff s psychosis, mania, anxiety disorders, or phobic disorders, learning or memory disorders (such as amnesia and age-related memory loss), attention deficit disorder, dysthymic disorder, major depressive disorder, mania, obsessive-compulsive disorder, psychoactive substance use disorders, anxiety, phobias, panic disorder, bipolar affective disorder, psychogenic pain syndromes, and eating disorders. Other examples of neurological disorders include injuries to the nervous system due to an infectious disease (such as meningitis, high fevers of various etiologies, HIV, syphilis, or post-polio syndrome) and injuries to the nervous system due to electricity (including contact with electricity or lightning, and complications from electro-convulsive psychiatric therapy). The developing brain is a target for neurotoxicity in the developing central nervous system through many stages of pregnancy as well as during infancy and early childhood, and the methods of the invention may be utilized in preventing or treating neurological deficits in embryos or fetuses in utero, in premature infants, or in children with need of such treatment, including those with neurological birth defects. Further neurological disorders include, for example, those listed in Harrison's Principles of Internal Medicine (Braunwald et al., McGraw-Hill, 2001) and in the American Psychiatric Association's Diagnostic and Statistical Manual of Mental Disorders DSM-IV (American Psychiatric Press, 2000) both incorporated herein by reference in their entirety. Neurological disorders associated with ophthalmic conditions include retina and optic nerve damage, glaucoma and age related macular degeneration.

The term "stroke" is art recognized and is intended to include sudden diminution or loss of consciousness, sensation, and voluntary motion caused by rupture or obstruction (for example, by a blood clot) of an artery of the brain.

"Traumatic brain injury" is art recognized and is intended to include the condition in which, a traumatic blow to the head causes damage to the brain or connecting spinal cord, often without penetrating the skull. Usually, the initial trauma can result in expanding hematoma, subarachnoid hemorrhage, cerebral edema, raised intracranial pressure, and cerebral hypoxia, which can, in turn, lead to severe secondary events due to low cerebral blood flow.

The term "outgrowth" includes the process by which axons or dendrites extend from a neuron. The outgrowth can result in a new neuritic projection or in the extension of a previously existing cellular process. Axonal outgrowth may include linear extension of an axonal process by 5 cell diameters or more. Neuronal growth processes, including neuritogenesis, can be evidenced by GAP-43 expression detected by methods such as immunostaining. "Modulating axonal outgrowth" means stimulating or inhibiting axonal outgrowth to produce salutatory effects on a targeted neurological disorder.

The term "CNS neurons" is intended to include the neurons of the brain, the cranial nerves and the spinal cord.

Various aspects of the invention are described in further detail in the following subsections:

Pharmaceutically Acceptable Formulations

Pharmaceutical compositions and packaged formulations comprising a hexose derivative and a pharmaceutically acceptable carrier are also provided by the invention. These pharmaceutical compositions may also include a macrophage-derived factor and/or a cAMP modulator.

In a method of the invention, the hexose derivative (e.g., mannose), optionally in conjunction with a macrophage-derived factor and/or a cAMP modulator, can be administered in a pharmaceutically acceptable formulation. Such pharmaceutically acceptable formulation may include the hexose derivative as well as a pharmaceutically acceptable carrier(s) and/or excipient(s). As used herein, "pharmaceutically acceptable carrier" includes any and all solvents, dispersion media, coatings, antibacterial and anti fungal agents, isotonic and absorption delaying agents, and the like that are physiologically compatible. For example, the carrier can be suitable for injection into the cerebrospinal fluid. Excipients include pharmaceutically acceptable stabilizers and disintegants. The present invention pertains to any pharmaceutically acceptable formulations, including synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes.

In one embodiment, the pharmaceutically acceptable formulations comprise a polymeric matrix. The terms "polymer" or "polymeric" are art-recognized and include a structural framework comprised of repeating monomer units which is capable of delivering a hexose derivative such that treatment of a targeted condition, such as a neurological disorder, occurs. The terms also include co-polymers and homopolymers such as synthetic or naturally occurring. Linear polymers, branched polymers, and cross-linked polymers are also meant to be included.

For example, polymeric materials suitable for forming the pharmaceutically acceptable formulation employed in the present invention, include naturally derived polymers such as albumin, alginate, cellulose derivatives, collagen, fibrin, gelatin, and polysaccharides, as well as synthetic polymers such as polyesters (PLA, PLGA), polyethylene glycol, poloxomers, polyaphydrides, and pluronics. These polymers are biocompatible with the nervous system, including the central nervous system, they are biodegradable within the central nervous system without producing any toxic byproducts of degradation, and they possess the ability to modify the manner and duration of the active compound release by manipulating the polymer's kinetic characteristics. As used herein, the term "biodegradable" means that the polymer will degrade over time by the action of enzymes, by hydrolytic action and/or by other similar mechanisms in the body of the subject. As used herein, the term "biocompatible" means that the polymer is compatible with a living tissue or a living organism by not being toxic or injurious and by not causing an immunological rejection. Polymers can be prepared using methods known in the art.

The polymeric formulations can be formed by dispersion of the active compound within liquefied polymer, as described in U.S. Pat. No. 4,883,666, the teachings of which are incorporated herein by reference or by such methods as bulk polymerization, interfacial polymerization, solution polymerization and ring polymerization as described in Odian G., Principles of Polymerization and ring opening polymerization, 2nd ed., John Wiley & Sons, New York, 1981, the contents of which are incorporated herein by reference. The properties and characteristics of the formulations are controlled by varying such parameters as the reaction temperature, concentrations of polymer and the active compound, the types of solvent used, and reaction times.

The active therapeutic compound can be encapsulated in one or more pharmaceutically acceptable polymers, to form a microcapsule, microsphere, or microparticle, terms used herein interchangeably. Microcapsules, microspheres, and microparticles are conventionally free-flowing powders consisting of spherical particles of 2 millimeters or less in diameter, usually 500 microns or less in diameter. Particles less than 1 micron are conventionally referred to as nanocapsules, nanoparticles or nanospheres. For the most part, the difference between a microcapsule and a nanocapsule, a microsphere and a nanosphere, or microparticle and nanoparticle is size; generally there is little, if any, difference between the internal structure of the two. In one aspect of the present invention, the mean average diameter is less than about 45 µm, preferably less than 20 µm, and more preferably between about 0.1 and 10 µm.

In another embodiment, the pharmaceutically acceptable formulations comprise lipid-based formulations. Any of the known lipid-based drug delivery systems can be used in the practice of the invention. For instance, multivesicular liposomes, multilamellar liposomes and unilamellar liposomes can all be used so long as a sustained release rate of the encapsulated active compound can be established. Methods of making controlled release multivesicular liposome drug delivery systems are described in PCT Application Publication Nos: WO 9703652, WO 9513796, and WO 9423697, the contents of which are incorporated herein by reference.

The composition of the synthetic membrane vesicle is usually a combination of phospholipids, usually in combination with steroids, especially cholesterol. Other phospholipids or other lipids may also be used.

Examples of lipids useful in synthetic membrane vesicle production include phosphatidylglycerols, phosphatidylcholines, phosphatidylserines, phosphatidylethanolamines, sphingolipids, cerebrosides, and gangliosides, with preferable embodiments including egg phosphatidylcholine, dipalmitoylphosphatidylcholine, distearoylphosphatidyleholine, dioleoylphosphatidylcholine, dipalmitoylphosphatidylglycerol, and dioleoylphosphatidylglycerol.

In preparing lipid-based vesicles containing an active compound such variables as the efficiency of active compound encapsulation, lability of the active compound, homogeneity and size of the resulting population of vesicles, active compound-to-lipid ratio, permeability, instability of the preparation, and pharmaceutical acceptability of the formulation should be considered.

Prior to introduction, the formulations can be sterilized, by any of the umerous available techniques of the art, such as with gamma radiation or electron beam sterilization.

Ophthalmic products for topical use may be packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v"). Such preparations may be packaged in dropper bottles or tubes suitable for safe administration to the eye, along with instructions for use.

Administration of the Pharmaceutically Acceptable Formulation

The pharmaceutically acceptable formulations of the invention are administered such that the active compound comes into contact with a subject's nervous system to thereby produce a neurosalutary effect. Both local and systemic administration of the formulations are contemplated by the invention. Desirable features of local administration include achieving effective local concentrations of the active compound as well as avoiding adverse side effects from systemic administration of the active compound. In one embodiment, the active compound is administered by introduction into the cerebrospinal fluid of the subject. In certain aspects of the invention, the active compound is introduced into a cerebral ventricle, the lumbar area, or the cistema magna. In another aspect, the active compound is introduced locally, such as into the site of nerve or cord injury, into a site of pain or neural degeneration, or intraocularly to contact neuroretinal cells.

The pharmaceutically acceptable formulations can be suspended in aqueous vehicles and introduced through conventional hypodermic needles or using infusion pumps.

In one embodiment, the active compound formulation described herein is administered to the subject in the period from the time of, for example, an injury to the CNS up to about 100 hours after the injury has occurred, for example within 24, 12, or 6 hours from the time of injury.

In another embodiment of the invention, the active compound formulation is administered into a subject intrathecally. As used herein, the term "intrathecal administration" is intended to include delivering an active compound formulation directly into the cerebrospinal fluid of a subject, by techniques including lateral cerebroventricular injection through a burrhole or cistemal or lumbar puncture or the like (described in Lazorthes et al., 1991, and Ommaya A. K., 1984, the contents of which are incorporated herein by reference). The term "lumbar region" is intended to include the area between the third and fourth lumbar (lower back) vertebrae. The term "cistema magna" is intended to include the area where the skull ends and the spinal cord begins at the back of the head. The ten-n "cerebral ventricle" is intended to include the cavities in the brain that are continuous with the central canal of the spinal cord. Administration of an active compound to any of the above mentioned sites can be achieved by direct injection of the active compound formulation or by the use of infusion pumps. Implantable or external pumps and catheter may be used.

For injection, the active compound formulation of the invention can be formulated in liquid solutions, preferably in physiologically compatible buffers such as Hank's solution or Ringer's solution. In addition, the active compound formulation may be formulated in solid form and re-dissolved or suspended immediately prior to use. Lyophilized forms are also included. The injection can be, for example, in the form of a bolus injection or continuous infusion (such as using infusion pumps) of the active compound formulation.

In one embodiment of the invention, the active compound formulation is administered by lateral cerebroventricular injection into the brain of a subject, preferably within 100 hours of when an injury (resulting in a condition characterized by aberrant axonal outgrowth of central nervous system neurons) occurs (such as within 6, 12, or 24 hours of the time of the injury). The injection can be made, for example, through a burr hole made in the subject's skull. In another embodiment, the formulation is administered through a surgically inserted shunt into the cerebral ventricle of a subject, preferably within 100 hours of when an injury occurs (such as within 6, 12 or 24 hours of the time of the injury). For example, the injection can be made into the lateral ventricles, which are larger, even though injection into the third and fourth smaller ventricles can also be made. In yet another embodiment, the active compound formulation is administered by injection into the cisterna magna, or lumbar area of a subject, preferably within 100 hours of when an injury occurs (such as within 6, 12, or 24 hours of the time of the injury).

An additional means of administration to intracranial tissue involves application of compounds of the invention to the olfactory epithelium, with subsequent transmission to the olfactory bulb and transport to more proximal portions of the brain. Such administration can be by nebulized or aerosolized prerparations.

In another embodiment of the invention, the active compound formulation is administered to a subject at the site of injury, preferably within 100 hours of when an injury occurs (such as within 6, 12, or 24 hours of the time of the injury).

In a further embodiment, ophthalmic compositions of the present invention are used to prevent or reduce damage to retinal and optic nerve head tissues, as well as to enhance functional recovery after damage to ocular tissues. Ophthalmic conditions that may be treated include, but are not limited to, retinopathies (including diabetic retinopathy and retrolental fibroplasia), macular degeneration, ocular ischemia, glaucoma. Other conditions to be treated with the methods of the invention include damage associated with injuries to ophthalmic tissues, such as ischemia reperfusion injuries, photochemical injuries, and injuries associated with ocular surgery, particularly injuries to the retina or optic nerve head by exposure to light or surgical instruments. The ophthalmic compositions may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The ophthalmic compositions may also be used prophylactically, especially prior to ocular surgery or noninvasive ophthalmic procedures or other types of surgery.

Duration and Levels of Administration

In a preferred embodiment of the method of the invention, the active compound is administered to a subject for an extended period of time to produce a neurosalutary effect, such as effect modulation of axonal outgrowth. Sustained contact with the active compound can be achieved by, for example, repeated administration of the active compound over a period of time, such as one week, several weeks, one month or longer. More preferably, the pharmaceutically acceptable formulation used to administer the active compound provides sustained delivery, such as "slow release" of the active compound to a subject. For example, the formulation may deliver the active compound for at least one, two, three, or four weeks after the pharmaceutically acceptable formulation is administered to the subject. Preferably, a subject to be treated in accordance with the present invention is treated with the active compound for at least 30 days (either by repeated administration or by use of a sustained delivery system, or both).

As used herein, the term "sustained delivery" is intended to include continual delivery of the active compound in vivo over a period of time following administration, preferably at least several days, a week, several weeks, one month or longer. Sustained delivery of the active compound can be demonstrated by, for example, the continued therapeutic effect of the active compound over time (such as sustained delivery of the macrophage-derived factor can be demonstrated by continued production of a neurosalutary effect in a subject). Alternatively, sustained delivery of the active compound may be demonstrated by detecting the presence of the active compound in vivo over time.

Preferred approaches for sustained delivery include use of a polymeric capsule, a minipump to deliver the formulation, a bioerodible implant, or implanted transgenic autologous cells (as described in U.S. Pat. No. 6,214,622). Implantable infusion pump systems (such as Infusaid; see such as Zierski, J. et al, 1988; Kanoff, R. B., 1994) and osmotic pumps (sold by Alza Corporation) are available in the art. Another mode of administration is via an implantable, externally programmable infusion pump. Suitable infusion pump systems and reservoir systems are also described in U.S. Pat. No. 5,368,562 by Blomquist and U.S. Pat. No. 4,731,058 by Doan, developed by Pharmacia Deltec Inc.

It is to be noted that dosage values may vary with the severity of the condition to be alleviated. It is to be further understood that for any particular subject, specific dosage regimens should be adjusted over time according to the individual need and the professional judgment of the person administering or supervising the administration of the active compound and that dosage ranges set forth herein are exemplary only and are not intended to limit the scope or practice of the claimed invention.

The invention, in another embodiment, provides a pharmaceutical composition consisting essentially of a hexose derivative and a pharmaceutically acceptable carrier, as well as methods of use thereof to modulate axonal outgrowth by contacting CNS neurons with the composition. By the term "consisting essentially of" is meant that the pharmaceutical composition does not contain any other modulators of neuronal growth such as, for example, nerve growth factor (NGF). In one embodiment, the pharmaceutical composition of the invention can be provided as a packaged formulation. The packaged formulation may include a pharmaceutical composition of the invention in a container and printed instructions for administration of the composition for producing a neurosalutary effect in a subject having a neurological disorder. Use of a hexose derivative in the manufacture of a medicament for modulating the axonal outgrowth of neurons is also encompassed by the invention.

In Vitro Treatment of CNS Neurons

Neurons derived from the central or peripheral nervous system can be contacted with a hexose derivative in vitro to modulate axonal outgrowth in vitro. Accordingly, neurons can be isolated from a subject and grown in vitro, using techniques well known in the art, and then treated in accordance with the present invention to modulate axonal outgrowth. Briefly, a neuronal culture can be obtained by allowing neurons to migrate out of fragments of neural tissue adhering to a suitable substrate (such as a culture dish) or by disaggregating the tissue, such as mechanically or enzymatically, to produce a suspension of neurons. For example, the enzymes trypsin, collagenase, elastase, hyaluronidase, DNase, pronase, dispase, or various combinations thereof can be used. Methods for isolating neuronal tissue and the disaggregation of tissue to obtain isolated cells are described in Freshney, Culture of Animal Cells, A Manual of Basic Technique, Third Ed., 1994, the contents of which are incorporated herein by reference.

Such cells can be subsequently contacted with a hexose (alone or in combination with a macrophage-derived factor and/or a cAMP modulator) in amounts and for a duration of time as described above. Once modulation of axonal outgrowth has been achieved in the neurons, these cells can be re-administered to the subject, such as by implantation.

Screening Assays

The ability of a hexose to produce a neurosalutary effect in a subject may be assessed using any of a variety of known procedures and assays. For example, the ability of a hexose derivative to re-establish neural connectivity and/or function after an injury, such as a CNS injury, may be determined histologically (either by slicing neuronal tissue and looking at neuronal branching, or by showing cytoplasmic transport of dyes). The ability of compounds of the invention to re-establish neural connectivity and/or function after an injury, such as a CNS injury, may also be assessed by monitoring the ability of the hexose derivative to fully or partially restore the electroretinogram after damage to the neural retina or optic nerve; or to fully or partially restore a pupillary response to light in the damaged eye.

Other tests that may be used to determine the ability of a hexose to produce a neurosalutary effect in a subject include standard tests of neurological function in human subjects or in animal models of spinal injury (such as standard reflex testing, urologic tests, urodynamic testing, tests for deep and superficial pain appreciation, propnoceptive placing of the hind limbs, ambulation, and evoked potential testing). In addition, nerve impulse conduction can be measured in a subject, such as by measuring conduct action potentials, as an indication of the production of a neurosalutary effect.

Animal models suitable for use in the assays of the present invention include the rat model of partial transaction (described in Weidner et al., 2001). This animal model tests how well a compound can enhance the survival and sprouting of the intact remaining fragment of an almost fully-transected cord. Accordingly, after administration of the hexose these animals may be evaluated for recovery of a certain function, such as how well the rats may manipulate food pellets with their forearms (to which the relevant cord had been cut 97%).

Another animal model suitable for use in the assays of the present invention includes the rat model of stroke (described in Kawamata et al., 1997). This paper describes in detail various tests that may be used to assess sensorimotor function in the limbs as well as vestibulomotor function after an injury. Administration to these animals of the compounds of the invention can be used to assess whether a given compound, route of administration, or dosage provides a neurosalutary effect, such as increasing the level of function, or increasing the rate of regaining function or the degree of retention of function in the test animals.

Standard neurological evaluations used to assess progress in human patients after a stroke may also be used to evaluate the ability of a hexose to produce a neurosalutary effect in a subject. Such standard neurological evaluations are routine in the medical arts, and are described in, for example, "Guide to Clinical Neurobiology" Edited by Mohr and Gautier (Churchill Livingstone Inc. 1995).

For assessing function of the peripheral nervous system, standard tests include electromyography, nerve conduction velocity measurements, potentials assessment and upper/lower extremity somato-sensory evoked potentials. Electromyography tests record the electrical activity in muscles, and is used to assess the function of the nerves and muscles. The electrode is inserted into a muscle to record its electrical activity. It records activity during the insertion, while the muscle is at rest, and while the muscle contracts. The nerve conduction velocity test evaluates the health of the peripheral nerve by recording how fast an electrical impulse travels through it. A peripheral nerve transmits information between the spinal cord and the muscles. A number of nervous system diseases may reduce the speed of this impulse. Electrodes placed on the skin detect and record the electrical signal after the impulse travels along the nerve. A second stimulating electrode is sends a small electrical charge along the nerve; the time between the stimulation and response will be recorded to determine how quickly and thoroughly the impulse is sent.

Standard tests for function of the cranial nerves, as known to those skilled in the neurological medical art, include facial nerve conduction studies; orbicularis oculi reflex studies (blink reflex studies); trigeminal-facial nerve reflex evaluation as used in focal facial nerve lesions, Bell's palsy, trigeminal neuralgia and atypical facial pain; evoked potentials assessment; visual, brainstem and auditory evoked potential measurements; thermo-diagnostic small fiber testing; and computer-assisted qualitative sensory testing.

The invention is further illustrated by the following examples, which should not be construed as further limiting. The contents of all references, patents and published patent applications cited throughout this application are hereby incorporated by reference.

EXAMPLES

Example I

Retinal Ganglion Cells Extend Axons in Response to Treatment with Hexose

Goldfish retinal ganglion cells are prepared as described in PCT application serial no. PCT/US98/03001, the contents of which are incorporated herein by reference, and contacted with a hexose derivative such as mannose. The ability of the hexose derivative to stimulate axonal outgrowth from the goldfish retinal ganglion cells is monitored as described in PCT application serial no. PCT/US98/03001.

Example II

Methods

Extraction low molecular weight factor from rat vitreous. Molecules present in the rat vitreous were extracted into normal saline (8 vitreous bodies in 1.5 ml saline, overnight with mixing, 4° C.). The vitreous bodies were derived from either normal adult male Fisher rats (Charles River Laboratories, Wilmington, Mass.), 200-250 g, or from rats 7 days after lens injury, a time at which we see clear evidence of GAP-43 upregulation in RGCs after lens injury (Leon et al., 2000). Lens injury was accomplished using a 30 G needle as described (Leon et al., 2000). The vitreous extract was passed through a 22 µM low-protein binding filter (Pall Life Sciences, Ann Arbor, Mich.) to remove cellular debris; low molecular components were separated by ultrafiltration through a 3 kDa molecular weight cut-off (MWCO) membrane.

Bovine vitreous fluid was extracted from the eyes of newborn calves in a ratio of 4 volumes normal saline to 1 volume of vitreous fluid. Extraction took place at 4° C. As above, extracts were passed through a 22 µM low protein binding filter (Pall), then a 3 kDa cut-off ultrafiltration device to remove higher molecular weight components. To determine whether a small molecule from the bovine vitreous behaves like goldfish AF-1 or inosine in promoting growth, we tested its activity in the presence or absence of 6-thioguanine (6-TG, 20 µM, Sigma), an antagonist of a purine-sensitive kinase that is important for axon growth or 4-(nitrobenzyl-6-thioinosine) (NBTI, 20 µM, Aldrich Chemicals), an inhibitor or purine transport across the cell membrane.

Fractionation of conditioned media. To concentrate the active factor(s) and remove inorganic salts, the low molecular weight extract of bovine vitreous was lyophilized and extracted with 95% ethanol (16% of the original sample volume, 4° C., with frequent Vortexing, 1 hr). The ethanol-soluble fraction was lyophilized, redissolved in 400 µL water, and applied to a C18 reversed-phase HPLC column (Delta Pak 5µ C 18 100 Å, Waters, Milford, Mass.: 0.5 ml/min). Buffer A was 0.1% trifluoroacetic acid (TFA) in water, whereas buffer B was 0.08% TFA in a mixture of isopropanol, acetonitrile and water in a ratio of 3:2:2. The gradient for elution was 0% B for 2 minutes and then 0-100% B in 42 minutes. Bioassays were performed on pools of fractions representing 2 min.

Further separation was achieved by gel-filtration chromatography using a Sephadex G-10 (Sigma) column 1.6 cm×48 cm. This column separates molecules under 700 Daltons. The sample was concentrated 20×, insoluble components were removed by centrifugation, and the soluble portion, which was found to contain all of the biological activity (not shown), was applied in a volume of 0.5 ml. The column was run under pressure at 0.3 ml/min using a peristaltic pump. Fractions of 4.5 ml were collected and tested in the bioassay at a concentration of approximately 5% relative to the original concentration in the sample.

The final stage of purification was achieved using a normal-phase HPLC column (Shodex aminopropyl, Thomson Instruments, Oceanside, Calif.). The fraction from the G-10 column containing axon-promoting activity was lyophilized and redissolved in 200 µl 80% acetonitrile. After pre-equilibrating the column with 75% acetonitrile, the sample was applied at a flow rate of 1 ml/min. Fractions of 1 ml were collected and bioassayed.

Goldfish retinal ganglion cell cultures. Mammalian AF-1 was initially characterized in bioassays using dissociated goldfish retinal ganglion cells (RGCs). In brief, Comet variety goldfish (Mt. Parnell Fisheries, PA) were dark-adapted, cooled to 4° C., and killed by cervical transection. Retinas were dissected and dissociated by incubation in papain followed by a series of trituration steps that result in an RGC-enriched cell suspension (Schwartz & Agranoff,; Schwalb et al., 1995). Approximately 500 RGCs per well were plated together with the experimental samples to be tested in defined, serum-free media containing Leibovitz' L15 media (Gibco BRL) plus N1 and N2 supplements (Bottenstein, Saito), antioxidants, and bovine serum albumin as described in detail elsewhere (Schwalb et al., 1995). In each experiment, 4 wells of each sample were distributed in 24-well plates in a blinded fashion so that the person evaluating axon outgrowth was unaware of the type of sample present in each well. Experiments included a positive control (previously validated goldfish AF-1 or inosine) and a negative control (defined media alone), likewise distributed on the plate in quadruplicate in a blinded fashion. After 6 days in culture at 21° C., axon outgrowth, operationally defined as the percent of RGCs that extended an axon≧5 cell diameters in length, was evaluated in approximately 150 consecutively encountered RGCs per well. Data were analyzed by averaging axon growth in the 4 wells for each sample, subtracting the level of growth found in negative controls (typically 3-5%), and normalizing by the net growth in positive controls (usually 20-40%). Data are presented as normalized means ± SEM. All experiments were repeated at least 3 times.

Rat retinal ganglion cell cultures. Retinal ganglion cells were identified by retrograde labeling with Fluorogold (FG: Fluorochrome, Inc.). For this, adult male Sprague-Dawley rats were anesthetized, placed in a stereotaxic apparatus, and the superior colliculi were exposed by removing the overlying posterior cerebral cortex. FG was injected into several sites in the superior colliculi bilaterally. In addition, a small piece of Gelfoam (Upjohn, Kalamazoo, Mich.) impregnated with FG was placed over the superior colliculi, the scalp wound closed, and the skin sutured closed. After allowing 7 days for FG to be retrogradely transported up the optic nerve, rats were killed, eyes were removed, and the retinas dissected. Retinas were dissociated with papain treatment followed by trituration. Mixed cultures containing 100-150 FG-labeled RGCs per well were maintained in 24 well plates in a defined, serum-free media (Minimal Essential Media containing $NaHCO_3$,) at 37° C. at 5% $CO_2$ for 3 days. As with the goldfish cultures, all experimental samples were tested in quadruplicate and were distributed across the culture dishes in a randomized fashion. Statistical handling of the data was as described above.

Mass spectrometry. FAB mass spectra were obtained at the Michigan State University Mass Spectrometry Facility using a JEOL. HX-110 double-focusing mass spectrometer (JEOL USA, Peabody, Mass.) operating in the positive or negative ion mode. Ions were produced by bombardment with a beam of Xe atoms (6 keV). The accelerating voltage was 10 kV and the resolution was set at 3000. For FAB-CAD-MS/MS, helium was used s the collision gas in a cell located in the first field-free region. The helium pressure was adjusted to reduce the abundance of the parent ion by 50%. A data system generated linked scans at a constant ratio of magnetic to electrical fields (B/E). The instrument was scanned from m/z 50 to 2000. Spectra presented were from a single scan.

Results

Figure 1A:
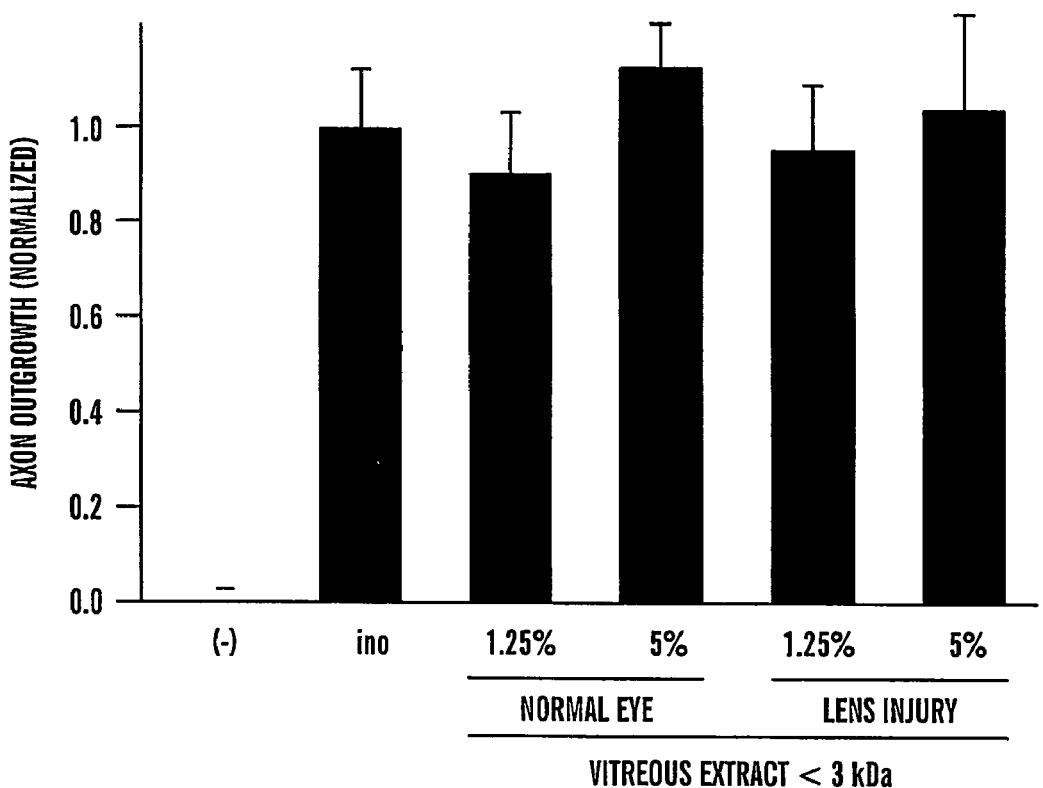
FIGS. 1A-B show axon-promoting effects of a low molecular weight factor from the rat vitreous humor.
Figure 1B:
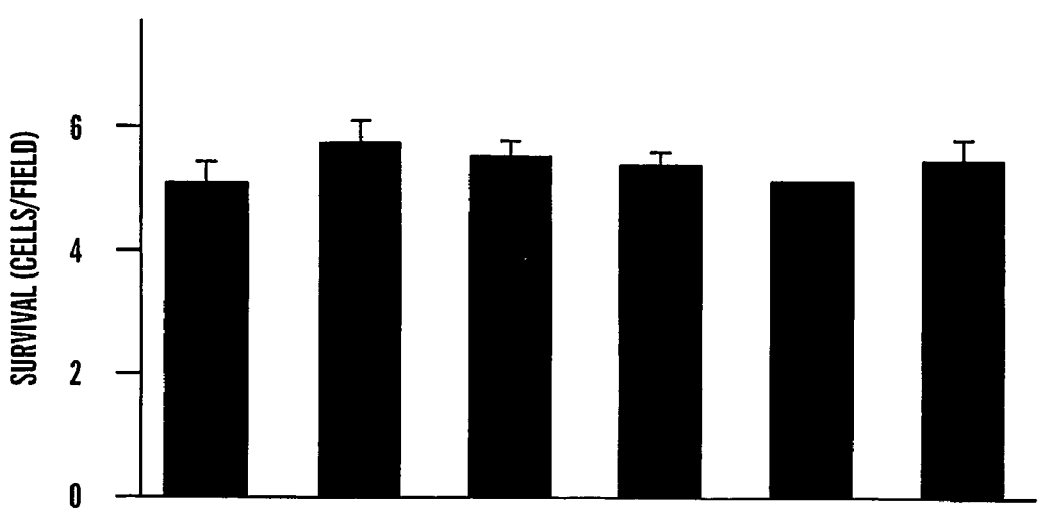

A small axon-promoting factor is constitutively present in the mammalian vitreous. Lens injury stimulates retinal ganglion cells to regenerate injured axons through the optic nerve in vivo (Leon et al., 2000). To investigate the factors that might stimulate this growth, we extracted the molecules that are present in the normal vitreous body, or in the vitreous body one week after nerve crush and lens injury, into saline. Molecules smaller than 3 kDa were separated by ultrafiltration and tested for axon-promoting activity using goldfish retinal ganglion cells as a bioassay (Schwalb et al., 1995; Benowitz et al., 1998). The low molecular weight extract showed full activity when diluted 80-fold, regardless of whether or not the lens had been injured (FIG. 1). At one-tenth this concentration, it was ineffective (data not shown).

Figure 2:
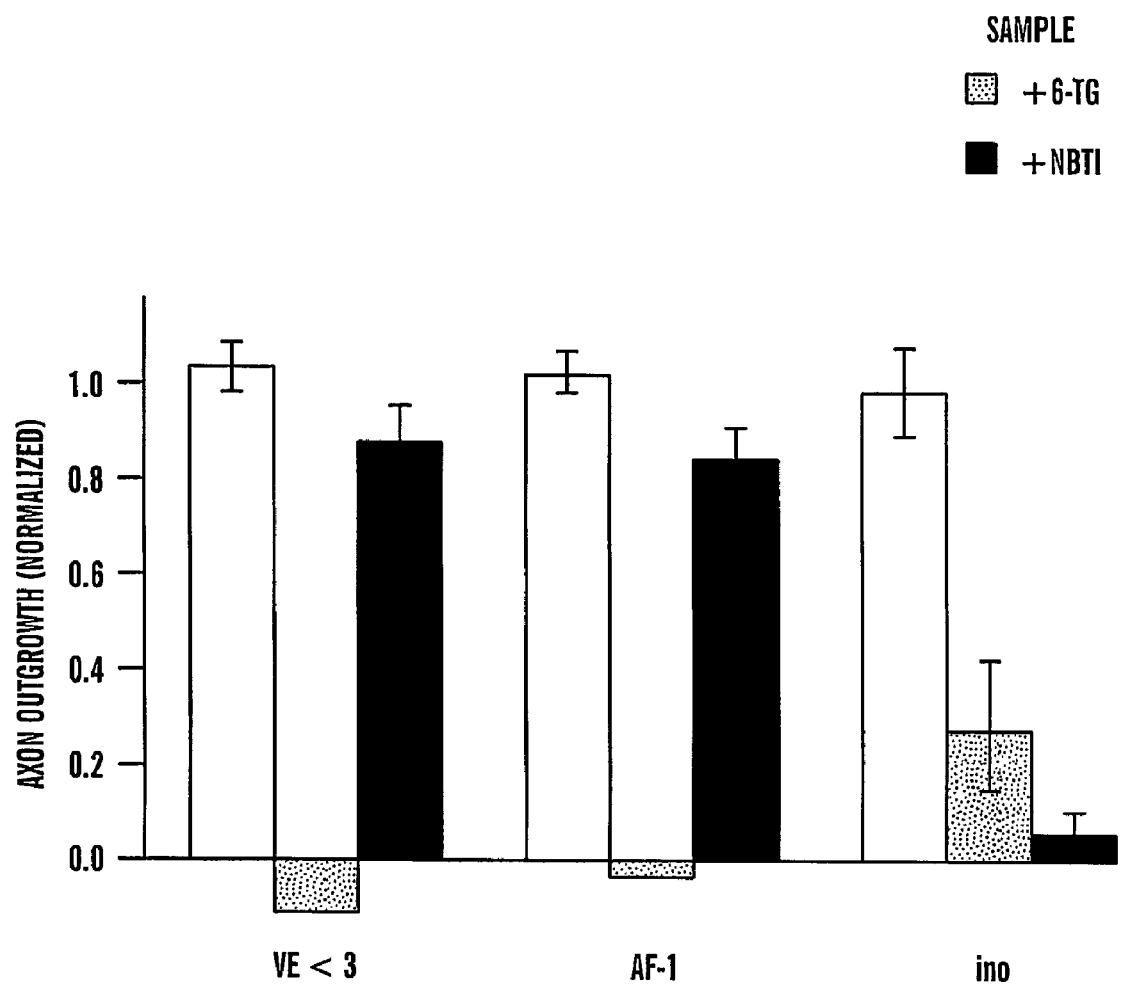
FIG. 2 shows properties of the low molecular weight vitreous-derived factor.

The small axon-promoting factor is present in bovine vitreous and behaves like goldfish AF-1. To isolate sufficient quantities of the small growth factor and analyze its structure, we investigated whether it was present in the bovine vitreous. A low molecular weight component of the bovine vitreous extract (VE<3), when tested at an 80-fold dilution, induced as much outgrowth from goldfish RGCs as goldfish-derived AF-1 (FIG. 2). To determine whether the vitreous-derived factor behaves like AF-1, we examined whether its activity could be blocked by either of two agents: 6-thioguanine, which non-competitively blocks the effect of AF-1 on outgrowth but which is competitive with inosine (Petrausch et al., 2000); or NBTI, an inhibitor of purine transport across the cell membrane, which blocks the effects of inosine but does not diminish the activity of AF-1 (Benowitz et al., 1998). NBTI had very little effect on growth induced by VE<3 or AF-1, but effectively blocked growth induced by inosine. In contrast, 6-TG brought growth induced by VE<3 or AF-1 below baseline levels, but only partially blocked the effects of inosine (FIG. 2). Thus, the low molecular weight factor from the vitreous behaves like goldfish AF-1.

The small vitreous-derived factor stimulates axon regeneration in adult rat RGCs in a cAMP-dependent manner. Retinas of adult rats were dissociated and cultured as described in Materials and Methods; RGCs were identified by virtue of retrograde labeling with Fluorogold prior to preparing the cultures. In the absence of additional factors, approximately 5%-8% of RGCs extended axons>2 cell diameters in length after 3 days. Elevating intracellular cAMP with forskolin or with the membrane permeable, nonhydrolyzable cAMP analog Sp-cAMPs had little effect on outgrowth. The low molecular weight extract from the vitreous stimulated a small but significant level of growth on its own (p<0.01), and the combination of this small factor with either forskolin or Sp-cAMPs greatly potentiated this effect (FIG. 3a: p<0.001 comparing growth with the low molecular weight factor plus either forskolin or Sp-cAMPs with the growth obtained with any one alone). As shown above for goldfish ROCs, 6-TG reduced growth induced by the low-molecular weight factor plus forskolin (p<0.01) or by the low molecular weight factor plus Sp-cAMPs (p<0.05). Thus, the low molecular weight factor from the vitreous stimulates rat RGCs to extend axons in a cAMP-dependent fashion; like axon growth in goldfish RGCs, outgrowth is mediated through a purine-sensitive mechanism. The effects of the low molecular weight fragment were unrelated to any changes in cell survival (FIG. 3b). Maximal effects were attained even when VE<3 was diluted to 4% of its original concentration in the vitreous (FIG. 3c).

Unlike rat RGCs, goldfish RGCs showed a robust response to VE<3 even without increasing intracellular $[cAMP]_i$ (FIG. 4). Neither forskolin (10 µM) nor Sp-cAMPs (150 µM) induced growth on its own, in conformity with previous results showing that membrane-permeable analogs of cAMP or cGMP do not stimulate goldfish RGCs to extend axons (Benowitz, 1998). When added to AF-1, forskolin and Sp-cAMPs caused a non-statistically significant decrease in outgrowth. Conversely, growth induced by AF-1 was not diminished by the membrane-permeable, nonhydrolyzable PKA antagonist Rp-cAMPs (100 µM) nor the PKA inhibitor H89 (5 µM). At 20 µM, H89 diminished the effect of AF-1 (p<0.001), although at this concentration H-89 affects other kinases besides PKA. Thus, the response of goldfish RGCs to the low molecular weight factor is considerably less cAMP-dependent than the response of rat RGCs.

Isolation of the active component. The low molecular weight fraction of the vitreous extract was concentrated by lyophilization and extracted into a small volume of 95% ethanol. This resulted in nearly complete recovery of the axon-promoting activity while removing approximately 98% of the inorganic salts (data not shown). Following separation on a reversed-phase C18 column, the axon-promoting activity was not retained by the column and eluted as part of a large absorbance peak in the first few minutes (FIG. 5a,b).

Further purification was achieved by gel-filtration chromatography on a Sephadex G-10 column. The axon-promoting activity was largely contained within a single fraction (165-180 min) that overlapped with a major absorbance peak (FIG. 5c, 5d). Even at high concentrations, this fraction induced only 60-80% the level of axon-promoting activity as the starting material. Material that elutes later on the G-10 column and which has no activity by itself, when added back to the active fraction, brings its activity back to the level of the starting material (data not shown). When the active fraction from the G-10 column was applied to a normal-phase column (LC-$NH_2$), the activity eluted late, in a region that showed very little absorbance (FIG. 5e, 5f). Thus, normal-phase chromatography resulted in a high degree of purification. The active fraction again stimulated about 80% as much outgrowth as the positive control (starting material). This fraction was concentrated and run again on the same column, collecting fractions coinciding with absorbance peaks visualized with the detector set at the highest level of UV sensitivity. Bioassay revealed that the axon-promoting activity was concentrated in a single peak eluting at 9.8 min (data not shown).

Identification of the active factor by mass spectrometry. The purified fractions containing the axon-promoting activity and adjacent inactive peaks were analyzed in the positive and negative ion modes by Fast Atom Bombardment (FAB) mass spectrometry. Principal results were obtained in the presence of glycerol and were confirmed in the presence of tetraethylammonium and nitrobenzoic acid. In the negative ion mode, the active fraction (#17) contained an ion with m/z=179.2 (arrow) that was absent in the adjacent inactive fraction (#16) (FIGS. 6a, b). Because m/z values in the negative ion mode correspond to the true mass minus 1 proton, the molecule present in the active fraction is predicted to have a mass of 180. In the positive ion mode, two peaks appeared in the biologically active fraction that were absent in the adjacent inactive fraction (m/z=273.2 and 255.2: FIGS. 6c, d, arrows). Because m/z values in the positive ion mode contain an additional proton, the two unique ions are predicted to have masses of 272.2 and 254.2; however, if these ions represent glycerol adducts (mass=92) of the parent species, the mass of the larger one would be 180, which is similar to that found in the negative ion mode, while the other would be 162. Further analysis of the m/z=273 ion by MS/MS in the positive ion mode (FIG. 6e) confirmed the presence of glycerol (m/z=93, asterisk) and the 180 mass (m/z=181, double arrows). MS/MS also generated peaks corresponding to the parent species minus multiples of 18, i.e., 163, 145, and 127 (arrows). The latter peaks are likely to represent serial losses of hydroxyl groups from the 181 ion, whereas the peaks with m/z=255 and 237 probably represent glycerol adducts of the 163 and 145 ions, respectively. These results predict that the active molecule is a carbohydrate with the formula $C_6H_{12}O_6$ (mass=180).

Specific carbohydrates induce axon regeneration from goldfish RGCs Based upon the mass spectrometry results, we tested the axon-promoting effects of hexose sugars and related compounds on RGCs in culture. In goldfish RGCs, myo-inositol, the ketoses fructose and sorbose, and the aldoses D-allose, D-altrose, D-gulose, D-talose, and D-galactose all failed to stimulate outgrowth (all tested at 50 or 100 µM: FIG. 7a). However, the two structurally related aldose sugars mannose and glucose stimulated as much outgrowth as the low molecular weight factor isolated from the bovine vitreous extract via gel-exclusion and normal-phase chromatography (c.f. FIG. 5d, f). The L-enantiomers of glucose and mannose were inactive (data not shown). Outgrowth in response to mannose saturated at 25-50 µM, and the $ED_{50}$ was approximately 10 µM (FIG. 7c). A similar dose-response curve was obtained for glucose (data not shown). As mentioned above, the growth-promoting factor derived from bovine vitreous retained only 60-80% of the original activity after isolation by size-exclusion and normal-phase chromatography (FIG. 5d,f), and full activity could be restored by adding back a later fraction from the size-exclusion column which itself did not cause any growth. Similarly, adding the same late-eluting fraction from the size-exclusion column to 50 µM mannose or glucose increased activity back to the level of the vitreous extract prior to fractionation (FIG. 7d). The effect of glucose (FIG. 7e) or mannose (not shown) on goldfish RGCs was not enhanced with the membrane-permeable, non-hydrolyzable cAMP analog dBcAMP. Conversely, the protein kinase A inhibitor KT5720, at the normally effective dosage of 1 µM, did not diminish the effect of mannose, and had only a slight effect at 10 µM (FIG. 7f). Likewise, the PKA inhibitor Rp-cAMPs had no effect on glucose-induced outgrowth at the normally effective dose of 100 µM, but blocked growth by 48% when tested at 1 mM (not shown).

The culture media used in these experiments already provides high concentrations of galactose (5 mM) and pyruvate (5 mM) for energy metabolism and as a carbon source. Thus, the outgrowth induced by low micromolar concentrations of mannose or glucose is unlikely to be related to energy metabolism. This is further suggested by the fact that adding 5 mM methyl pyruvate, which is readily used for ATP synthesis to our media, had no effect (data not shown). Further evidence that the effects of glucose and mannose on axon growth are unrelated to energy metabolism comes from the fact that low micromolar concentrations of these carbohydrates have no effect on cell survival (FIG. 7b).

To examine the specificity of the observed effects and to gain insights into possible structure-function relationships, we examined the biological activity of several related compounds. The L-enantiomers of glucose and mannose were completely inactive (FIG. 8a). D-glucosamine was strongly active (p<0.001); D-mannosamine was ineffective, as were 2-deoxy-D-glucose, 3-O-methyl-D-glucose, methyl-α-D-glucopyranoside, methyl-β-D-glucopyranoside, acetylglucosamine and fucose. D-glucose- and D-mannose-6-phosphate stimulated a relatively modest but statistically significant amount of outgrowth (p<0.01). Because these latter two phosphate derivatives carry a negative charge, they do not pass through the cell membrane. This would suggest that glucose and mannose may stimulate axon outgrowth via an extracellular mechanism. Further support for this possibility comes from studies using the inhibitor of glucose transport, 3-O-methyl glucose (3-O-MG). In a molar ratio of 100:1, 3-O-MG failed to block the effects of glucose (FIG. 8b). We also investigated the effects of another glucose transport inhibitor, 2-deoxyglucose (2-DG). However, at concentrations as low as 1 mM, 2-DG had nonspecific effects on axon growth, and blocked the effects of both glucose and inosine; inosine has been shown to stimulate axon growth via an intracellular mechanism (Benowitz et al., 1998. As shown above, the effect of AF-1 on goldfish RGCs is not enhanced by elevating intracellular cAMP levels using either forskolin or Sp-cAMP-s, and actually appears to decline (FIG. 4). Likewise, the effect of glucose on goldfish RGCs is diminished by the addition of forskolin (FIG. 8c).

In several cell types, glucose is sensed by the activity of hexokinases, the first enzymes in the glycolytic pathway, or by the concentration of downstream metabolites (Rolland et al., 2001). In goldfish RGCs, mannoheptulose (MH, 10 mM), an inhibitor of both glucose-6 kinase and hexose-6 kinase, had no effect on outgrowth induced by glucose or mannose, despite being detrimental to cell survival (FIGS. 8d and 8e). Thus, the glucose/mannose sensor for axon growth is not the kinase involved in the first step of glycolysis, nor does it depend on the intracellular concentration of the 6-phosphate derivatives or of any downstream metabolites. The failure of MH to block outgrowth even in the face of diminished cell survival provides further evidence that the axon-promoting effect of D-glucose or D-mannose is unrelated to cell survival.

When introduced extracellularly, D-glucose-6-phosphate and D-mannose-6-phosphate stimulated a modest amount of outgrowth at 100 µM (p<0.01), and appreciable growth at 1 mM (p<0.001) (FIG. 8f). The 6-phosphate derivatives are negatively charged and do not pass through the cell membrane (Abeles et al., 1992). This suggests that the 6-phosphate derivatives, and by extension glucose and mannose themselves, may stimulate axon outgrowth via an extracellular sensor.

Rat RGCs respond selectively to mannose in a cAMP-dependent manner. Like goldfish RGCs, RGCs from the mature rat also grow axons in response to micromolar concentrations of monosaccharides, but with several interesting differences. Rat RGCs show a marginally significant response to either mannose (p=0.05, one-tailed) or VE<3 alone (p=0.05, two-tailed), and a small but significant response to forskolin alone (FIG. 9a). In the presence of forskolin, mannose in micromolar concentrations more than doubled the level axon growth induced by forskolin alone (p<0.001). Mannose-induced growth was at least as high as that induced by low molecular weight components of unfractionated bovine vitreous extract, and was not augmented further by the addition of high concentrations of glucose. In other studies, mannose was seen to achieve near-maximal effects at 50 µM (data not shown). In contrast, glucose, even at millimolar concentrations as occur in vivo and in the presence of forskolin failed to induce growth above the level of forskolin alone. FIG. 9b shows the effect is not related to cell survival. Thus, whereas goldfish RGCs extend lengthy axons in response to either glucose or mannose without augmenting intracellular cAMP, rat RGCs respond selectively to mannose in a cAMP-dependent manner.

RGCs from the mature rat showed a far greater response selectivity than goldfish RGCs. D-mannose by itself had little effect on rat RGCs (FIG. 9a and FIG. 9c), but in the presence of forskolin, it increased axon outgrowth 3-fold over baseline (p<0.001: FIGS. 9a and 9c). This effect was similar to that of VE<3 (c.f. FIG. 3), and was likewise unrelated to changes in cell survival (FIG. 9b and FIG. 9d). In the presence of forskolin, mannose elicited maximal effects by 50 µM, with an $ED_{50}$ of approximately 10 µM (data not shown). Stereospecificity is demonstrated by the inactivity of L-mannose (FIG. 9c). Under similar conditions, glucose had no effect whatsoever (FIG. 9c), even when present at millimolar concentrations (FIG. 9a). Of the other sugars tested, gulose had some activity (p<0.05) (FIG. 9c). Unlike goldfish RGCs, rat RGCs did not respond to glucosamine (FIG. 9c) or to high concentrations of mannose-6-phosphate (up to 10 mM: data not shown).

Additive effect of a macrophage-derived factor (s) and mannose in rat RGCs. In culture, a 10-20 kDa macrophage-derived protein potentiates the response of rat RGCs to a small vitreous-derived growth factor when [cAMP]i is elevated (Yin et al., 2003). In the presence of forskolin, macrophage-conditioned media nearly doubled the response of rat RGCs to mannose, elevating growth almost 6-fold above baseline (FIG. 9e). This growth corresponds to over 50% of cultured RGCs extending axons in 3 days.

Discussion

We show here that specific monosaccharides stimulate retinal ganglion cells to regenerate their axons, and that this effect is independent of energy metabolism. Even when other energy sources are abundant, goldfish RGCs respond to low micromolar concentrations of either glucose or mannose to regenerate their axons. Responsiveness to these carbohydrates does not require elevation of intracellular cAMP. Rat RGCs, on the other hand, are more selective. Rat RGCs extend axons in response to micromolar concentrations of mannose in a cAMP-dependent fashion, but not to glucose at levels similar to those found in vivo. The response of rat RGCs can be augmented considerably further by macromolecules secreted by macrophages. These findings may help explain in part the different regenerative capacities of lower and higher vertebrates in vivo. In the goldfish, the abundance of glucose may suffice to enable RGCs to regenerate their axons after injury. In the rat, however, although mannose is abundant in the vitreous humor, its' role in stimulating axon regeneration is likely to be permissive rather than a regulatory. By itself, mannose is insufficient to induce axon regeneration in vivo or in vitro. However, in the presence of elevated intracellular cAMP, mannose potentiates the effects of macrophage-derived factors, and hence is likely to play a role in the dramatic axon regeneration that is seen after macrophage activation in vivo (Yin et al., submitted).

In cell culture, media conditioned by the non-neuronal cells of the goldfish optic nerve was found to stimulate extensive axon regeneration from RGCs. Partial purification revealed that most of this activity could be attributed to a small, hydrophilic molecule that was termed AF-1 (Schwalb et al., 1995, 1996). In addition, in culture, AF-1 was shown to induce the expression of many of the gene products known to be associated with axon regeneration in vivo (Petrausch et al., 2000). As shown here, the mammalian vitreous fluid contains a small molecule with biophysical properties and bioactivity similar to those of goldfish AF-1. Both AF-1 and the vitreous-derived factor are hydrophilic, elute as a coherent peak on a gel-filtration column, and induce similar levels of axon growth from goldfish RGCs in a 6-thioguanine-sensitive and NBTI-insensitive fashion (this study; Schwab et al., 1996; and unpublished observations). Upon further purification, the low molecular weight factor from bovine vitreous was found to contain one component that carried most of the biological activity and a second component, which, although not sufficient to induce axon growth by itself, enhanced the effects of the active factor. Through a combination of ultrafiltration, differential solubility, gel-filtration chromatography, and normal-phase HPLC, we isolated the active component from the vitreous and found by mass spectrometry that it was a carbohydrate with the formula $C_6H_{12}O_6$. Testing multiple monosaccharides with this formula revealed a high degree of specificity for stimulating outgrowth. For goldfish RGCs, the position of the hydroxyl groups on carbon atoms 3-5 is highly constrained, as is stereospecificity, whereas on carbon 2, either the mannose or glucose configuration stimulates growth, as does the substitution of an amide group. The fact that low micromolar concentrations were required to stimulate growth even in the presence of high concentrations of pyruvate and galactose provides one indication that the axon-promoting effects of the monosaccharides are independent of energy metabolism. This is further indicated by the dissociation between cell survival and axon growth noted throughout the studies. Interestingly, mannose-6- and glucose-6-phospate also stimulated growth, though to a lesser extent than the monosaccharides themselves. Because the phosphate derivatives can not get into the cell, it is likely that they are acting upon an extracellular sensor. The possibility that glucose and mannose act extracellularly is further indicated by the observation that their effect on goldfish RGCs is not diminished by 3-O-methyl glucose, an inhibitor of glucose transport. An inhibitor of hexose kinases did not block the axogenic effects of glucose or mannose despite diminished cell survival. Together, these findings lend further support to the idea that the effects of glucose and mannose on ougrowth are likely to be through an extracellular sensor and to be independent of energy metabolism or intracellular conversion to another product. In mammalian RGCs, the dissociation between the axogenic and energetic roles of the carbohydrates is even clearer, since only mannose stimulated outgrowth; glucose at levels up to 5 mM had no axon-promoting effects.

Cyclic AMP may play several roles in facilitating axon growth. In neonatal rat RGCs, the ability of trophic factors to stimulate cell survival requires cAMP, which in at least some instances enables the cognate receptors to translocate from the cytoplasm to the cell membrane (Meyer-Franke et al., 1995; Shen et al., 1999; Goldberg et al., 2002). Even when the survival of RGCs is made trophic factor-independent by over-expression of the bcl-2 gene, RGCs still require elevated cAMP to be able to extend axons in response to trophic factor stimulation (Goldberg et al., 2002). In growth cones, intracellular cAMP levels have a rapid effect in determining whether various extracellular signals result in attraction or repulsion, and a delayed effect in mediating the "priming" effect of trophic factors for overcoming growth inhibition by myelin or specific myelin proteins (Cai et al, Neuron, ca. 1999). This latter effect of cAMP is protein-synthesis dependent, and is related to enhanced expression of Arginase I and its products, polyamines, which are sufficient to overcome myelin inhibition (Cai et al., 2002). In our studies, the role of cAMP is not likely to be related to polyamine synthesis, since our culture medium already contains high concentrations (100 µM) of putrescine. However, cAMP is required to enable mannose to upregulate expression of GAP-43. In the case of goldfish RGCs, outgrowth was not enhanced by elevating intracellular cAMP levels.

In summary, our results show that the low molecular weight factor that stimulates axon outgrowth in goldfish retinal ganglion cells and the low molecular weight factor that enhances the response of mature rat RGCs to other growth factors are monosaccharides. Goldfish RGCs show a relatively nonselective growth response to low micromolar concentrations of either glucose, mannose, or glucosamine, and this does not require elevation of intracellular cAMP. Thus, the great abundance of these sugars may help explain the efficient regeneration of the goldfish optic nerve that occurs spontaneously in vivo. In mammals, although regenerative failure has been ascribed to inhibitory myelin proteins and to the glial scar at the injury site, these barriers can be overcome to a large extent by intracellular manipulations that cause a macrophage influx into the eye (Berry et al., 1996; Leon et al., 2000; Fischer et al., 2000, 2001; Yin et al., 2003). Our finding that adult rat RGCs regenerate their axons in response to a macrophage-derived factor in the presence of mannose and elevated cAMP indicates that monosaccharides may also play an important role in axon regeneration in higher vertebrates.

The following Examples 3 and 4 are formulations useful for intraocular, periocular or retrobulbar injection or perfusion.

Example 3

| Component | % w/v |
|---|---|
| D-mannose | 0.1 |
| Dibasic sodium phosphate | 0.2 |
| HPMC | 0.5 |
| Polysorbate 80 | 0.05 |
| Benzalkonium chloride | 0.01 |
| Sodium chloride | 0.75 |
| Edetate disodium | 0.01 |
| NaOH/HCl | q.s. to pH 7.4 |
| Purified water | q.s. to 100% |
| Cremophor EL | 10 |

-continued

| Component | % w/v |
|---|---|
| Tromethamine | 0.12 |
| Boric acid | 0.3 |
| Mannitol | 4.6 |
| Edetate disodium | 0.1 |
| Benzalkonium chloride | 0.1 |
| NaOH/HCl | q.s. to pH 7.4 |
| Purified water | q.s. to 100% |

Example 4

| Component | % w/v |
|---|---|
| Oncomodulin | 0.1 |
| D-mannose | 0.1 |
| cAMP modulator | 0.1 |
| Dibasic sodium phosphate | 0.2 |
| HPMC | 0.5 |
| Polysorbate 80 | 0.05 |
| Benzalkonium chloride | 0.01 |
| Sodium chloride | 0.75 |
| Edetate disodium | 0.01 |
| NaOH/HCl | q.s. to pH 7.4 |
| Purified water | q.s. to 100% |
| Cremophor EL | 10 |
| Tromethamine | 0.12 |
| Boric acid | 0.3 |
| Mannitol | 4.6 |
| Edetate disodium | 0.1 |
| Benzalkonium chloride | 0.1 |
| NaOH/HCl | q.s. to pH 7.4 |
| Purified water | q.s. to 100% |

Equivalents

Those skilled in the art will recognize, or be able to ascertain using no more than routine experimentation, many equivalents to the specific embodiments of the invention described herein. Such equivalents are intended to be encompassed by the following claims.

REFERENCES

All references cited herein and throughout the specification are hereby incorporated by reference in their entirety.
1. Abeles R H, Frey P A, Jencks W P (1992) Biochemistry. Boston, Mass.: Jones and Bartlett.
2. Aguayo A J, Rasminsky M, Bray G M, Carbonetto S, McKerracher L, Villegas-Perez M P, Vidal-Sanz M, Carter D A (1991) Degenerative and regenerative responses of injured neurons in the central nervous system of adult mammals. Philos Trans R Soc Lond B Biol Sci 331:337-343.
3. Bastmeyer M, Beckmann M, Schwab M E, Stuermer C A (1991) Growth of regenerating goldfish axons is inhibited by rat oligodendrocytes and CNS myelin but not but not by goldfish optic nerve tract oligodendrocytelike cells and fish CNS myelin. J Neurosci 11:626-640.
4. Benowitz L I, Jing Y, Tabibiazar R, Jo S A, Petrausch B, Stuermer C A, Rosenberg P A, Irwin N (1998) Axon outgrowth is regulated by an intracellular purine-sensitive mechanism in retinal ganglion cells. J Biol Chem 273:29626-29634.
5. Berry M, Carlile J, Hunter A (1996) Peripheral nerve explants grafted into the vitreous body of the eye promote the regeneration of retinal ganglion cell axons severed in the optic nerve. J Neurocytol 25:147-170.

6. Bomze H M, Bulsara K R, Iskandar B J, Caroni P, Skene J H (2001) Spinal axon regeneration evoked by replacing two growth cone proteins in adult neurons. Nat Neurosci 4:38-43.
7. Cai D, Qiu J, Cao Z, McAtee M, Bregman B S, Filbin M T (2001) Neuronal cyclic AMP controls the developmental loss in ability of axons to regenerate. J Neurosci 21:4731-4739.
8. Cai D, Deng K, Mellado W, Lee J, Ratan R, Filbin M (2002) Arginase I and Polyamines Act Downstream from Cyclic AMP in Overcoming Inhibition of Axonal Growth MAG and Myelin In Vitro. Neuron 35:711.
9. Fischer D, Pavlidis M, Thanos S (2000) Cataractogenic lens injury prevents traumatic ganglion cell death and promotes axonal regeneration both in vivo and in culture. Invest Ophthalmol Vis Sci 41:3943-3954.
10. Fischer D, Heiduschka P, Thanos S (2001) Lens-injury-stimulated axonal regeneration throughout the optic pathway of adult rats. Exp Neurol 172:257-272.
11. Goldberg J L, Espinosa J S, Xu Y, Davidson N, Kovacs G T, Barres B A (2002) Retinal ganglion cells do not extend axons by default: promotion by neurotrophic signaling and electrical activity. Neuron 33:689-702.
12. Jacobson M (1991) Developmental Neurobiology, Third Edition. New York: Plenum.
13. Kanoff, R. B. (1994) J. Am. Osteopath. Assoc. 94:487-493.
14. Kawamata et al. (1997) Proc. Natl. Acad. Sci. USA 94(15):8179-8184.
15. Lazorthes et al. (1991) Advances in Drug Delivery Systems and Applications in Neurosurgery, 143-192.
16. Leon S, Yin Y, Nguyen J, Irwin N, Benowitz L I (2000) Lens injury stimulates axon regeneration in the mature rat optic nerve. J Neurosci 20:4615-4626.
17. Meyer-Franke A, Kaplan M R, Pfrieger F W, Barres B A (1995) Characterization of the signaling interactions that promote the survival and growth of developing retinal ganglion cells in culture. Neuron 15:805-819.
18. Ming G L, Song H J, Berninger B, Holt C E, Tessier-Lavigne M, Poo M M (1997) cAMP-dependent growth cone guidance by netrin-1. Neuron 19:1225-1235.
19. Nano et al., (2000) Pflugers Arch 439(5):547-54.
20. Neumann S, Woolf C J (1999) Regeneration of Dorsal Column Fibers into and beyond the Lesion Site following Adult Spinal Cord Injury. Neuron 23:83-91.
21. Neumann S, Bradke F, Tessier-Lavigne M, Basbaum A I (2002) Regeneration of sensory axons within the injured spinal cord induced by intraganglionic cAMP elevation. Neuron 34:885-893.
22. Ommaya A K, (1984) Cancer Drug Delivery, 1: 169-179.
23. Petrausch B, Tabibiazar R, Roser T, Jing Y, Goldman D, Stuermer C A, Irwin N, Benowitz L I
24. (2000) A purine-sensitive pathway regulates multiple genes involved in axon regeneration in goldfish retinal ganglion cells. J Neurosci 20:8031-8041.
25. Qiu J, Cai D, Dai H, McAtee M, Hoffman P N, Bregman B S, Filbin M T (2002) Spinal axon regeneration induced by elevation of cyclic AMP. Neuron 34:895-903.
26. Ramer M S, Priestley J V, McMahon S B (2000) Functional regeneration of sensory axons into the adult spinal cord [see comments]. Nature 403:312-316.
27. Ramon y Cajal S (1991) Degeneration and Regeneration of the Nervous System. New York: Oxford University Press.
28. Rolland F, Winderickx J, Thevelein J M (2001) Glucose-sensing mechanisms in eukaryotic cells. Trends Biochem Sci 26:310-317.
29. Schwalb J M, Boulis N M, Gu M F, Winickoff J, Jackson P S, Irwin N, Benowitz L I (1995) Two factors secreted by the goldfish optic nerve induce retinal ganglion cells to regenerate axons in culture. J Neurosci 15:5514-5525.
30. Schwalb J M, Gu M F, Stuenner C, Bastmeyer M, Hu G F, Boulis N, Irwin N, Benowitz L I (1996) Optic nerve glia secrete a low-molecular-weight factor that stimulates retinal ganglion cells to regenerate axons in goldfish. Neuroscience 72:901-910.
31. Schwartz M, Agranoff B W (1981) Outgrowth and maintenance of neurites from cultured goldfish retinal ganglion cells. Brain Res 206:331-343.
32. Shen S, Wiemelt A P, McMorris F A, Barres B A (1999) Retinal ganglion cells lose trophic responsiveness after axotomy [In Process Citation]. Neuron 23:285-295.
33. Sivron T, Schwab M E, Schwartz M (1994) Presence of growth inhibitors in fish optic nerve myelin: postinjury changes. Journal of Comparative Neurology 343:237-246.
34. Song H, Ming G, He Z, Lehmann M, McKerracher L, Tessier-Lavigne M, Poo M (1998) Conversion of neuronal growth cone responses from repulsion to attraction by cyclic nucleotides. Science 281:1515-1518.
35. Tolkovsky A M, Suidan H S (1987) Adenosine 5'-triphosphate synthesis and metabolism localized in neurites of cultured sympathetic neurons. Neuroscience 23:1133-1142.
36. Volonte C, Rukenstein A, Loeb D M, Greene L A (1989) Differential inhibition of nerve growth factor responses by purine analogues: correlation with inhibition of a nerve growth factor-activated protein kinase. J Cell Biol 109: 2395-2403.
37. Walker F, Patrick R S (1967) Constituent monosaccharides and hexosamine concentration of normal human vitreous humour. Exp Eye Res 6:227-232.
38. Wanner M, Lang D M, Bandtlow C E, Schwab M E, Bastmeyer M, Stuermer C A (1995) Reevaluation of the growth-permissive substrate properties of goldfish optic nerve myelin and myelin proteins. J Neurosci 15:7500-7508.
39. Weidner et al. (2001) Proc. Natl. Acad. Sci. USA 98:3513-3518.
40. Yin Y, Cui Q, Li Y, Irwin N, Fischer D, Harvey A R, Benowitz L I (2003) Macrophage-derived factors stimulate optic nerve regeneration. J Neurosci 23:2284-2293.
41. Zierski, J. et al (1988) Acta Neurochem. Suppl. 43:94-99.

We claim:

1. A method of promoting neuronal outgrowth in a neuron in a subject with retinal damage comprising contacting the neuron with an effective amount of D-mannose, to thereby promote neuronal outgrowth of the neuron.

2. The method of claim 1, further comprising contacting the neuron with forskolin.

3. The method of claims 1 or 2, further comprising contacting the neuron with oncomodulin.

4. The method of claims 1 or 2, further comprising contacting the neuron with TGF-β.

5. The method of claim 1, wherein the effective amount is sufficient to achieve an effective concentration of D-mannose at the neuron of from 5 μM to 1 mM.

6. The method of claim 1, wherein the effective amount is sufficient to achieve an effective concentration of D-mannose at the neuron of from 25 μM to 500 μM.

* * * * *